US012594249B2

(12) United States Patent
Kramer et al.

(10) Patent No.: US 12,594,249 B2
(45) Date of Patent: Apr. 7, 2026

(54) SOLUBLE CURCUMIN AND ITS DERIVATIVES

(71) Applicant: ThermoLife International, LLC, Signal Hill, CA (US)

(72) Inventors: Ronald Kramer, Signal Hill, CA (US); Alexandros Nikolaidis, Nea Kallikratia (GR)

(73) Assignee: ThermoLife International, LLC, Signal Hill, CA (US)

(*) Notice: Subject to any disclaimer, the term of this patent is extended or adjusted under 35 U.S.C. 154(b) by 0 days.

(21) Appl. No.: 18/732,567

(22) Filed: Jun. 3, 2024

(65) Prior Publication Data

US 2024/0398726 A1 Dec. 5, 2024

Related U.S. Application Data

(60) Provisional application No. 63/508,470, filed on Jun. 15, 2023, provisional application No. 63/470,712, filed on Jun. 2, 2023.

(51) Int. Cl.

| | |
|---|---|
| *A61K 31/12* | (2006.01) |
| *A61K 47/02* | (2006.01) |
| *A61P 19/02* | (2006.01) |
| *A61P 21/00* | (2006.01) |
| *A61P 29/00* | (2006.01) |

(52) U.S. Cl.

CPC .............. *A61K 31/12* (2013.01); *A61K 47/02* (2013.01); *A61P 19/02* (2018.01); *A61P 21/00* (2018.01); *A61P 29/00* (2018.01)

(58) Field of Classification Search

None

See application file for complete search history.

(56) References Cited

U.S. PATENT DOCUMENTS

| | | | | |
|---|---|---|---|---|
| 2010/0286100 A1* | 11/2010 | First | A61K 31/192 | 514/629 |
| 2023/0234934 A1* | 7/2023 | Domb | A61P 31/10 | 514/456 |

FOREIGN PATENT DOCUMENTS

| | | | |
|---|---|---|---|
| CN | 1438225 A * | 8/2003 | |
| CN | 114106823 | 3/2022 | |
| WO | 2008051474 | 5/2008 | |
| WO | WO-2015087259 A1 * | 6/2015 | A61K 31/12 |
| WO | 2021202872 | 10/2021 | |
| WO | 2022182523 | 9/2022 | |

OTHER PUBLICATIONS

English Translation of CN1438225 (Aug. 27, 2003).*

(Continued)

*Primary Examiner* — Bong-Sook Baek

(74) *Attorney, Agent, or Firm* — Booth Udall, PLC; Pacer K. Udall

(57) ABSTRACT

Disclosed is a composition including ammonia and curcumin or curcuminoid, such as an ammonium phenoxide of curcumin. Also disclosed is a method for forming an ammonium phenoxide of curcumin or curcuminoid including dissolving the curcumin or curcuminoid in an ammonia solution. Further disclosed is a method of treating a curcumin-improvable condition including administering an ammonium phenoxide of curcumin or curcuminoid to a subject.

17 Claims, 20 Drawing Sheets
(6 of 20 Drawing Sheet(s) Filed in Color)

(56) References Cited

OTHER PUBLICATIONS

Gustiani, S. H. et al., "Modification of curcumin from turmeric rhizome (*Curcuma longa*) extract through O-ethylation with K2CO3/TBAB catalyst to enhance its antibacterial activity", AIP Conference Proceedings, 2020, vol. 2242, 040006, pp. 1-7.

* cited by examiner

CURCUMIN

DEMETHOXYCURCUMIN

BISDEMETHOXYCURCUMIN

CYCLOCURCUMIN

SOLUBLE CURCUMIN AND ITS DERIVATIVES

CROSS-REFERENCE TO RELATED APPLICATIONS

The present application claims priority to and the benefit of U.S. Provisional Patent Application No. 63/470,712, filed Jun. 2, 2023, and U.S. Provisional Patent Application No. 63/508,470, filed Jun. 15, 2023, the contents of each of which are hereby incorporated by reference in their entireties.

FIELD

The disclosure relates to a process for preparing curcumin and curcuminoid formulations with improved solubility and bioavailability.

BACKGROUND

Curcumin is a bright yellow chemical produced by plants of the *Curcuma* species. It is the principal curcuminoid of turmeric (*Curcuma longa*), a member of the ginger family, Zingiberaceae. Chemically, curcumin is a diarylheptanoid, belonging to the group of curcuminoids, which are phenolic pigments responsible for the yellow color of turmeric. FIG. 1 depicts the chemical structure of curcumin. FIG. 2 depicts the chemical structures of curcumin metabolites. FIG. 3 depicts the chemical structure of certain exemplary curcuminoids.

Curcumin is sold as an herbal supplement, cosmetics ingredient, food flavoring, and food coloring. In spite of turmeric's long history of as a therapeutic in traditional Chinese and Indian medicine, no laboratory and clinical research have confirmed any medical use for curcumin. This is because it is difficult to study the effects of curcumin in human or even animal models. The compound is both unstable and poorly bioavailable. A major reason for its poor bioavailability is its poor solubility in water. In fact, curcumin is almost insoluble in pure water (0.6 μg/mL) at standard conditions, though its solubility in organic solvents such as ethanol at standard conditions is improved (1 mg/mL).

To date, numerous approaches have been undertaken to improve the bioavailability of curcumin. One approach is the use of an adjuvant, like piperine, that interferes with glucuronidation. Other approaches use a liposomal delivery strategy, nanoparticles, or a curcumin phospholipid complex. Use of structural analogues of curcumin (for example, EF-24) is another broad approach. And lastly, boiling curcumin in water is even another approach for improving its water solubility. FIG. 4 (reproduced from Tabanelli et al., *Pharmaceutics*. 2021, 13 (10): 1715) depicts exemplary approaches that try to improve the bioavailability of curcumin.

All current approaches suffer from drawbacks. Many of the delivery formulations shown in FIG. 4 have been discontinued due to being inadequate for commercial purposes. Some of the issues these formulations encountered are that they were too expensive and too difficult to produce, unstable under environmental conditions, and used ingredients not suitable for food applications.

Thus, new strategies are needed to provide an economical and simple to produce method that uses FDA food approved excipients and ingredients to improve the bioavailability of curcumin.

SUMMARY OF THE INVENTION

In attempting to create a novel curcumin formulation, multiple experiments using various organic bases were utilized. The organic bases included creatine, creatinine, arginine, lysine, histidine, methylamine, ethylamine, propylamine, butylamine, pentylamine, hexylamine, heptylamine, diethylamine, spermidine, putrescine, trimethylamine, isobutylamine, isoamylamine, pyrrolidine, cadaverine, agmatine, phenethylamine, hordenine, trigonelline, carnitine, choline, glycocyamine, guanidine, methylguanidine and dimethylguanidine. After all this undue exhausting experimentation only the ammoniac phenoxide was found to procure a stable complex with curcumin with improved solubility. Thus, a method of producing an ammonium phenoxide of curcumin or curcuminoids (and related substances) with ammonia and formulations thereof with improved solubility and dissolution properties is described.

The success of the disclosed method is surprising as stable solid conjugate would be theoretically impossible due to phenols being not very acidic and ammonia being a weak base. The impossibility is even greater if the powder is subjected to vacuum, with ammonia being a gas. In predicting the equilibrium of phenol and ammonia versus phenoxide and ammonium in an aqueous solution, ammonium has a lower pKa than phenol (9.25 to phenol's 9.95), making ammonium comparatively more acidic. Thus, the reaction to form phenoxide and ammonium is theoretically energetically unfavorable and ammonia cannot deprotonate phenols.

The method of producing a phenoxide of curcumin or curcuminoid (and related substances) comprises dissolving curcumin or curcuminoid in an aqueous (or other suitable solvent) ammonia solution in a molar ratio of at least 1:1 curcumin or curcuminoid to ammonia or preferably a molar ratio of 1:2 curcumin or curcuminoid to ammonia; drying said solution preferably at 60° C. or lower, preferably under vacuum till a dry product of orange-yellow color exists; and grinding formed complex into powder. In some implementations, the method further comprises mixing said powder with a dissolution enhancer such as sodium carbonate.

In some implementations of the method, the ammonia solution comprises about 5 wt % to about 40 wt % ammonia.

In some aspects, the ammonium phenoxide of curcumin or curcuminoid are described. The contemplated molecular formula for the ammonium phenoxide of curcumin is as follows:

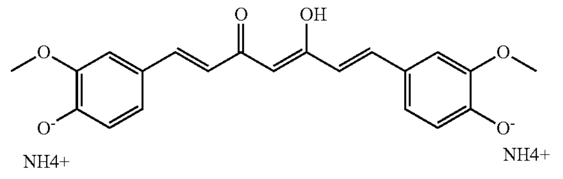

The calculated molar mass is 402.442 g/mol, which has been experimentally confirmed by weighing of the finished product.

If less than 1:2 curcumin to ammonia ratio is used, such as a 1:1 ratio, then the monophenoxide forms:

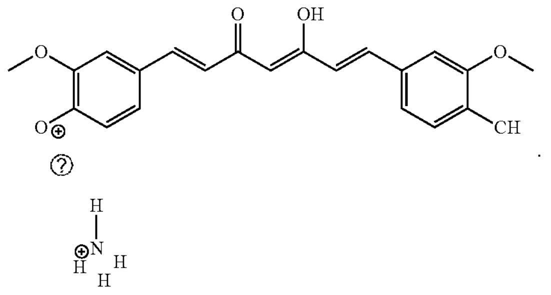

The contemplated ammonium phenoxides of curcumin metabolites are as follows:

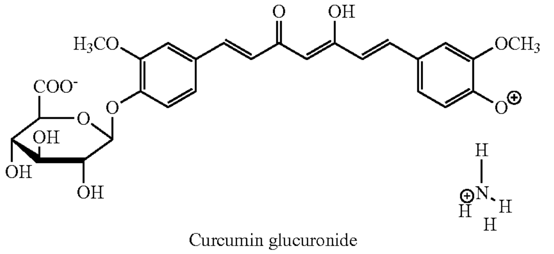

Curcumin glucuronide

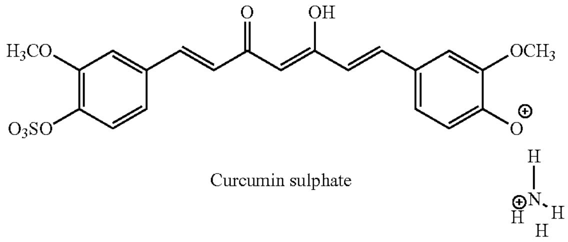

Curcumin sulphate

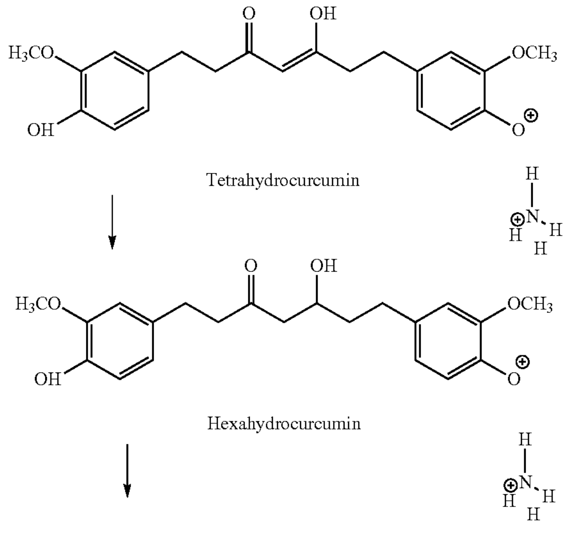

Tetrahydrocurcumin

Hexahydrocurcumin

-continued

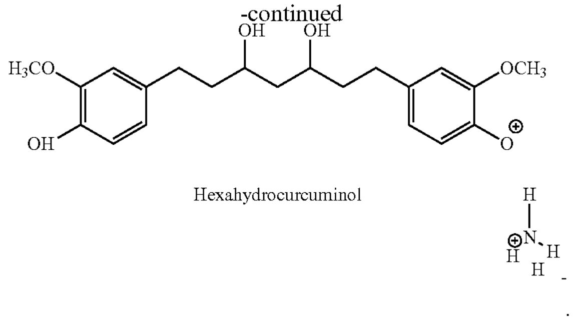

Hexahydrocurcuminol

The contemplated ammonium phenoxides of some curcumin derivatives are as follows:

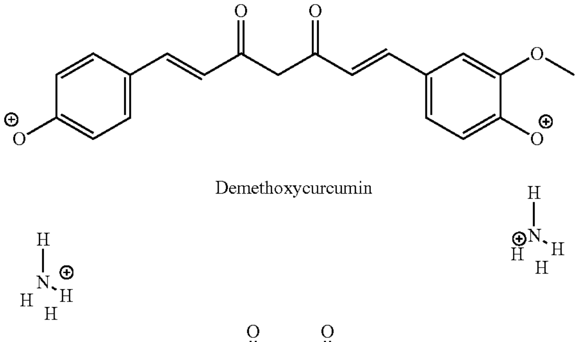

Demethoxycurcumin

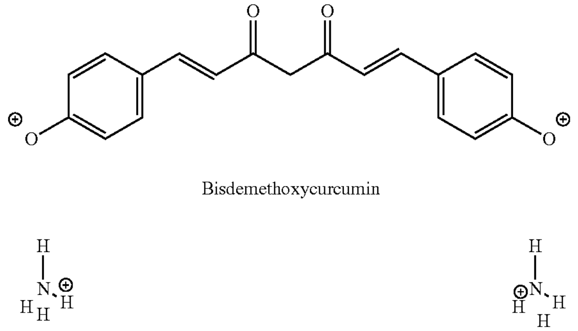

Bisdemethoxycurcumin

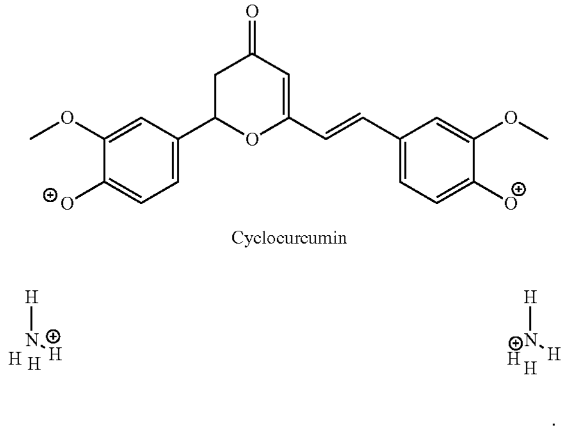

Cyclocurcumin

Also disclosed is a composition comprising ammonia and curcumin or a curcuminoid (for example, tetrahydrocurcumin). In some aspects of the composition, the ammonia and curcumin or curcuminoid form an ammonium phenoxide of curcumin or an ammonium phenoxide of curcuminoid.

A method of treating a curcumin-improvable condition is further described. The method comprising administering an ammonium phenoxide of curcumin or curcuminoid to a subject. In some implementations, the subject is administered the curcumin ammonium phenoxide or ammonium phenoxide of curcumin metabolites at a dose of 1-30,000 mg per day. The dose of curcumin ammonium phenoxide or ammonium phenoxide of curcumin metabolites may be administered in multiple doses per day. The mode of administration may be topical, transdermal, oral, rectal, ophthalmic, nasal, vaginal, and/or parenteral. In certain implementations, the subject is orally administered the curcumin ammonium phenoxide or ammonium phenoxide of curcumin metabolites to treat a curcumin-improvable condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Implementations will hereinafter be described in conjunction with the appended and/or included DRAWINGS, where like designations denote like elements.

DETAILED DESCRIPTION

Figure 1:
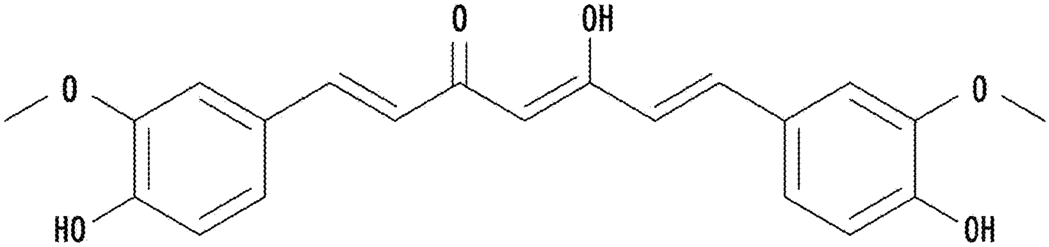
FIG. 1 depicts the chemical structure of curcumin.
Figure 2:
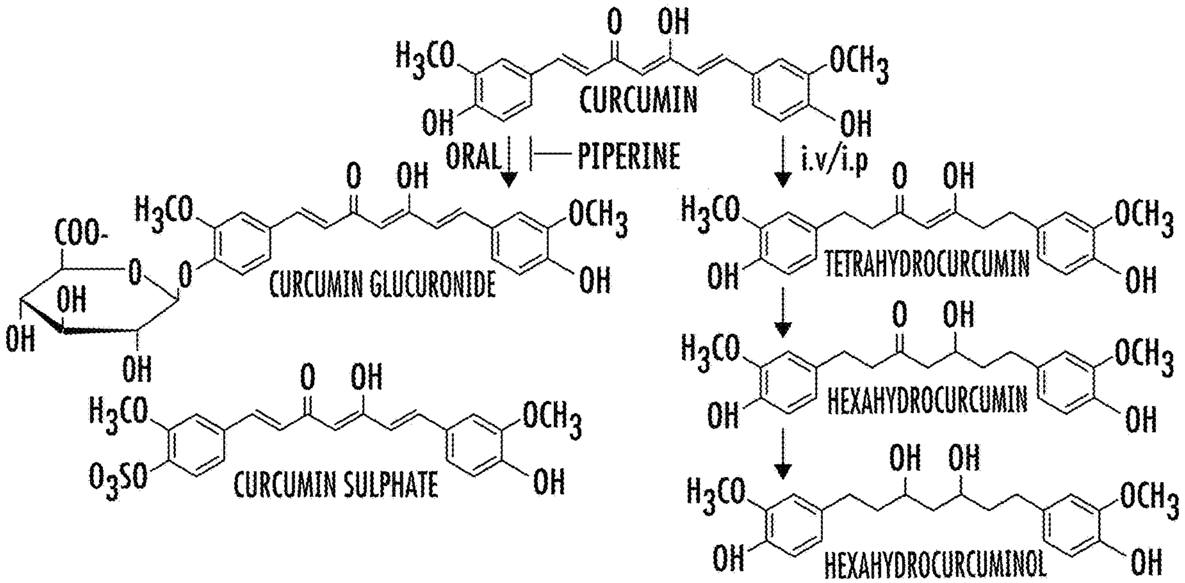
FIG. 2 depicts the chemical structures of curcumin metabolites.
Figure 3:
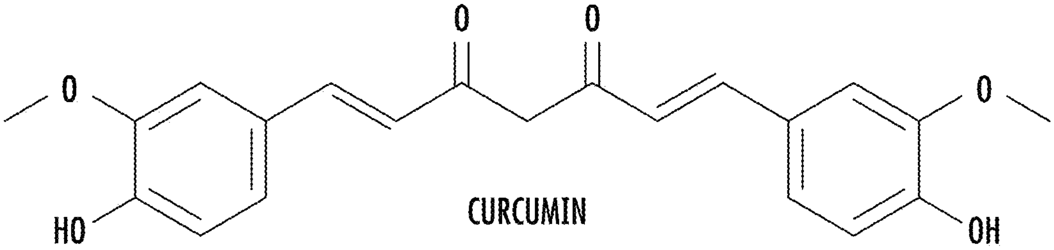
FIG. 3 depicts the chemical structure of certain exemplary curcuminoids.
Figure 3:
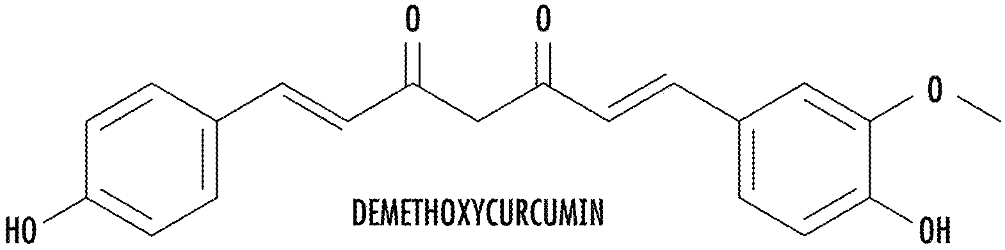
Figure 3:
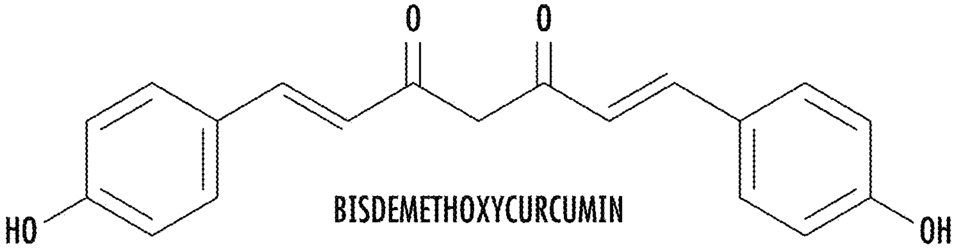
Figure 3:
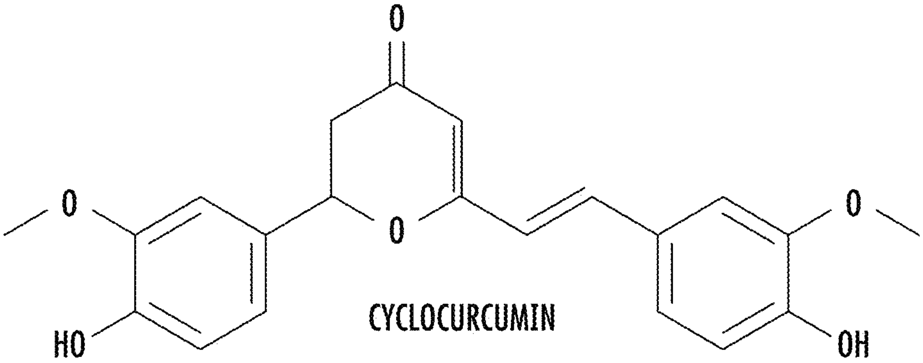
Figure 4:
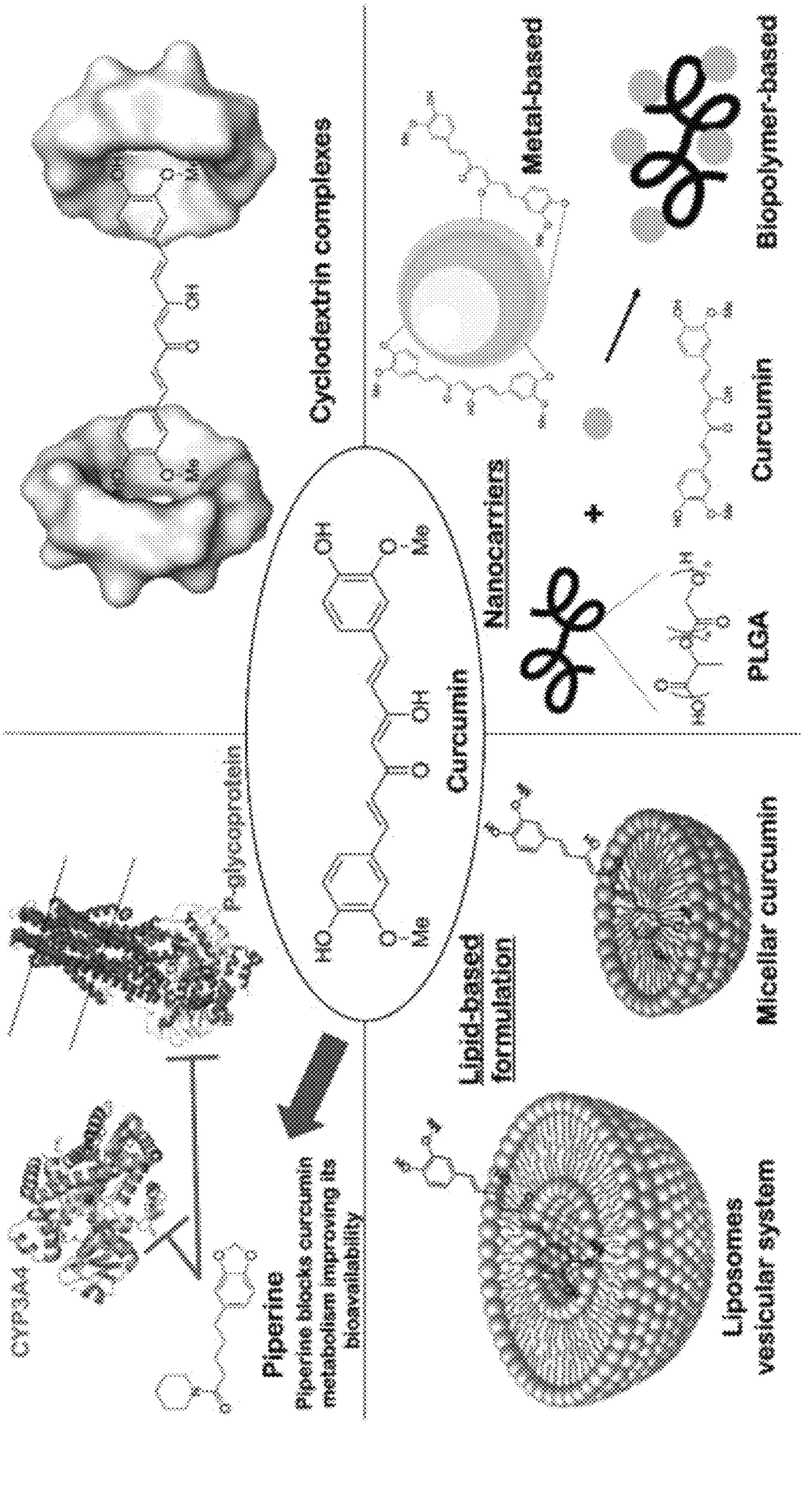
FIG. 4 depicts exemplary approaches that try to improve the bioavailability of curcumin, which is reproduced from Tabanelli et al., *Pharmaceutics.* 2021, 13 (10): 1715.

Detailed aspects and applications of the disclosure are described in the drawings and detailed description of the disclosure. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that the present disclosure may be practiced without these specific details. It should be noted that there are many different and alternative configurations, devices, and technologies to which the disclosed disclosures may be applied. The full scope of the disclosures is not limited to the examples that are described below.

The singular forms “a,” “an,” and “the” include plural referents unless the context clearly dictates otherwise. Thus, for example, reference to “a step” includes reference to one or more of such steps.

It will be understood that the term “curcumin” refers to the molecule of curcumin itself (also known as diferuloylmethane), which can be isolated from plants or synthetically produced, and its metabolites or derivatives. By non-limiting example, reference to “curcumin” herein includes curcumin glucuronide, curcumin sulphate, tetrahydrocurcumin, hexahydrocurcumin, hexahydrocurcuminol, demethoxycurcumin, bisdemethoxycurcumin dimethyl-curcumin, hydrazinocurcumin, and curcumin metallic complexes such as with copper and magnesium.

As used herein, the term “curcuminoid” refers to curcuminoids other than curcumin, which can be isolated in plants or synthetically produced, and its metabolites or derivatives. By non-limiting example, reference to “curcuminoid” herein includes, demethoxycurcumin, bisdemethoxycurcumin, cyclocurcumin, and curcuminoid metallic complexes such as with copper and magnesium.

As used herein, "pharmaceutically acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, dilutant, a hydrogen bonding agent, a flavoring agent, a flow agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, crosscarmelose cellulose, magnesium stearate, and silicon dioxide.

As used in this document, "pharmaceutically effective" is a phrase used in its broadest sense, including, by non-limiting example, effective in a clinical trial or for a specific patient. When used in a method claim, pharmaceutically effective will mean in a dose enough to achieve the claim's preamble.

As used in this document, "pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

As used herein, the term "human saliva" will be understood by its common physiological meaning, which is a thick, normally colorless (with the exception of some disorders), opalescent fluid that is constantly present in the human mouth. Human saliva comprises water, mucus, proteins, mineral salts, and amylase. As saliva circulates in the mouth cavity it picks up food debris, bacterial cells, and white blood cells as well as dissolves compounds that can dissolve in water, such as the compounds of this application. It can exist in the air through talking or coughing and can be a contaminant in foods supplements and medicine.

As used herein, the term "human gastric juice" will be understood by its common physiological meaning, which is a watery acidic fluid that aids digestion and is secreted by glands in the walls of the stomach. With the exception of enteric coated compounds, virtually all enteric coated compounds come in contact with gastric juice and a large part of them get at least partially dissolved.

As used herein, the term "human enteric fluid" (also known as "human enteric juice") will be understood by its common physiological meaning, which is a fluid that exists in the human intestines, usually containing the processed products of gastric juice as well as various other enzymes, bile and electrolytes that help with nutrient absorption.

The disclosure relates to the preparation of curcumin and curcuminoid formulations with better solubility and dissolution. The preparation method comprises dissolving curcumin or curcuminoid in an aqueous (or other suitable solvent) ammonia solution in a molar ratio of at least 1:1 curcumin or curcuminoid to ammonia, such as a molar ratio of 1:2 curcumin or curcuminoid to ammonia for example; drying said solution at 60° C. or lower, possibly under vacuum, till a dry product of orange-yellow color exists; and grinding the formed complex into powder. In some implementations, the method further comprises mixing said powder with a dissolution enhancer such as sodium carbonate. In some implementations of the method, the ammonia solution is about 5 wt % to about 40 wt % ammonia.

The disclosure also relates to compositions comprising an ammonium phenoxide of curcumin or curcuminoid (for example, tetrahydrocurcumin). In some implementations, the composition further comprises a dissolution enhancer, such as sodium carbonate for example. In some other implementations, the ammonium phenoxide of curcumin or curcuminoid is combined with a dietary ingredient, a food additive, and/or a pharmaceutically acceptable additive.

Supplements and ingredients that may be used in ammonium phenoxide of curcumin or curcuminoid compositions to enhance the effectiveness include but are not limited to: 1,3-DMAA, 1,3-DMBA, 1,4-Butanediol, 1,4-DMAA, 1-Androsterone, 1-Epiandrosterone, 19-nor-DHEA,4-Androsterone, 5-deca zol, 5-HTP, 5aOHP, 6-Bromo, 7,8-benzoflavone, 7-alpha-hydroxy-DHEA, 7-beta-hydroxy-DHEA, 7-Keto-DHEA, 7-Methoxyflavone, Abscess Root, Abuta, Acacia rigidula, Acai, Acerola, Acetyl-L-Carnitine, Ackee, Aconite, Activated Charcoal, Active hexose correlated compound (AHCC), Adenosine, Adrafinil, Adrenal extract, Adrue, Aegeline, African Wild Potato, Agar, *Agaricus* Mushroom, Agave, Agmatine, Agrimony, *Ajuga nipponensis*, Alanine, *Albizia julibrissin*, Alchemilla, Alder Buckthorn, Aletris, Alfalfa, Algal Oil, Algin, Alkanna, Allspice, Aloe, Alpha-GPC, Alpha-Ketoglutarate (AKG), Alpha-Linolenic Acid (ALA), Alpha-Lipoic Acid, Alpine Ragwort, Alpinia, Amaranth, Ambrette, American Adder's Tongue, American Chestnut, American Dogwood, American Elder, American *Ginseng*, American Hellebore, American Ivy, American Mistletoe, American Pawpaw, American Spikenard, American White Water Lily, Andarine, Andiroba, Andrographis, Androstenediol, Androstenedione, Androstenetrione, Androsterone, Angel's Trumpet, *Angelica archangelica*, Angostura, Anhydrous Crystalline Maltose, Anise, Annatto, Antineoplastons, Antioxidants, Apoaequorin, Apple, Apple Cider Vinegar, Apple Polyphenols, Apricot, Apricot Kernel, Arabinoxylan, *Arenaria Rubra*, Arimistane, Aristolochia, *Arnica*, Arrach, Arrowroot, Arsenic, *Artemisia Herba-Alba*, Artichoke, *Arum*, Asafoetida, Asarabacca, Ascophyllum nodosum, Ascorbigen, Ash, Ashitaba, Ashwagandha, Asian Water Plantain, Asparagus, Asparagus *Racemosus*, Aspartic Acid, Aspen, Astaxanthin, *Astragalus*, Atlantic Cedar, Atractylodes, Autumn *Crocus*, Avens, Avocado, Avocado soy unsaponifiables (ASU), Avocado Sugar Extract, Ayahuasca, Babassu, Bach Flower Remedies, *Bacillus Coagulans*, Bacopa, Bael, Baikal Skullcap, Ba Ji Tian, Bamboo, Banaba, Banana, Baobab, Barley, Basil, Bay Leaf, Bayberry, Bear's Garlic, Bee Pollen, Bee Venom, Beer, Beeswax, Beet, *Belladonna*, Benfotiamine, Benzoin, Berberine, Bergamot, Beta-Alanine, Beta-Carotene, Beta-Cryptoxanthin, Beta-Glucans, Beta-Hydroxybutyrate (BHB), Beta-Methylphenethylamine (BMPEA), Beta-Sitosterol, Betaine Anhydrous, Betaine Hydrochloride, *Betel* Nut, Beth root, Betony, *Bifidobacterium animalis* subsp, *lactis, Bifi-*

*dobacterium bifidum, Bifidobacterium breve, Bifidobacterium longum*, Bilberry, Biotin, Birch, Bishop's Weed, Bismuth, Bismuth Nitrate, Bistort, Bitter Almond, Bitter Melon, Bitter Milkwort, Bitter Orange, Bitter Yam, Bittersweet Nightshade, Black Alder, Black Bryony, Black Cohosh, Black Currant, Black Haw, Black Hellebore, Black Hoof Mushroom, Black Horehound, Black Mulberry, Black Mustard, Black Nightshade, Black Pepper, Black *Psyllium*, Black Raspberry, Black Rice, Black Root, Black Seed, Black Tea, Black Walnut, Blackberry, Blackthorn, Blessed Thistle, Blond *Psyllium*, Bloodroot, Blue Cohosh, Blue Flag, Blue-Green Algae, Blueberry, Bog Bilberry, Bog Labrador Tea, Bogbean, Bois de Rose Oil, Boldo, Boneset, Borage, Boron, Boswellia *Serrata*, Bovine Cartilage, Bovine Colostrum, Boxwood, Branched-chain Amino Acids (BCAA), Breadfruit, Brewer's Yeast, Brickellia, Bridelia, Broccoli, Broccoli Sprout, Bromelain, Brown Rice, Brussels Sprout, Bryonia, Buchu, Buck's-horn Plantain, Buckhorn Plantain, Buckwheat, Bugle, Bugleweed, Bulbine *natalensis*, Bulbous Buttercup, Bupleurum, Burdock, Burning Bush, Burr Marigold, Butcher's Broom, Butea Superba, Butterbur, Buttercup, Butternut, Butylated hydroxytoluene (BHT), Cabbage, Cade, Caffeic Acid, Caffeine, Cajeput Oil, Calabar Bean, Calabash Chalk, Calamint, Calamus, Calanus Oil, Calcium, Calcium D-Glucarate, Calea Zacatechichi, Calendula, California Poppy, Calotropis, Calumba, Camphor, Camu Camu, Canada Balsam, Canadian Fleabane, Canadian Hemp, Canaigre, *Cananga* Oil, Cannabichromene (CBC), Cannabidiol (CBD), Cannabidivarin (CBDV), Cannabigerol (CBG), Cannabinol (CBN), *Cannabis*, Canola Oil, Canthaxanthin, Capers, Caprylic Acid, *Capsicum*, Caralluma, Caraway, Carbon 60 (C60), Cardamom, Cardarine, Carlina, Carnosine, Carob, Carqueja, Carrageenan, Carrot, Cascara Sagrada, Cascarilla, Casein Peptides, Casein Protein, Cashew, Cassava, *Cassia Auriculata, Cassia* Cinnamon, *Cassia* Nomame, Cassie Absolute, Castor Bean, Castoreum, Cat's Claw, Cat's Foot, *Catechu*, Catnip, Catuaba, Cauliflower, Celery Centaury, *Cereus*, Cesium, Cetylated Fatty Acids (CFAs), Ceylon Cinnamon, Ceylon Leadwort, Cha de Bugre, Chaga, Chanca *Piedra*, Chaparral, Chaulmoogra, Cheken, Chelation Therapy Products, *Chenopodium* Oil, Chervil, Chia, Chickweed, Chicory, Chinese Cucumber, Chinese Mallow, Chinese Prickly Ash, Chirata, Chitosan, Chive, *Chlorella*, Chlorine Dioxide, Chlorophyll, Chlorophyllin, Chokeberry, Choline, Chondroitin Sulfate, Chromium, *Chrysanthemum*, Chrysin, Chuchuhuasi, Chymotrypsin, Cilantro, Cinchona, Cissus *Quadrangularis*, Cistanche *deserticola*, Citicoline, Citric Acid, Citronella oil, Clary Sage, Clay, *Clematis recta*, Clivers, Clove, Clown's Mustard plant, Clubmoss, Cnidium, Cobalt, Coca, Cocillana, Cocoa, Coconut, Coconut Oil, Coconut Water, Cod Liver Oil, Codonopsis, Coenzyme Q10, Coffee, Coffee Charcoal, Cola Nut, *Coleus*, Collagen Peptides, Collagen Type I (native), Collagen Type II (native), Collard, Colloidal Minerals, Colloidal Silver, Colocynth, Coltsfoot, Columbine, Combretum *micranthum*, Comfrey, Common Stonecrop, Condurango, Conjugated Linoleic Acid (CLA), Copaiba Balsam, Copper, Coral, *Cordyceps*, Coriander, Corkwood Tree, Corn Poppy, Corn Silk, Cornflower, Corydalis yanhusuo, Costus, Cotton, Couch Grass, Cowhage, Cowslip, Cramp bark, Cranberry, Creatine, Croton Seeds, Cubebs, Cucumber, Cudweed, Cumin, Cursed Buttercup, Cyanostane, Cyclamen, Cypress, D-Mannose, Daffodil, Damiana, Dandelion, Danshen, Date Palm, *Datura Wrightii*, Deanol, Deer Velvet, Delta-8-Tetrahydrocannabinol (Delta-8-THC), Delta-9-Tetrahydrocannabinol (THC), Dendrobium, Desert Parsley, Devil's Claw, Devil's Club, DHEA, Diacylglycerol, Diatomaceous earth, Diindolylmethane, Diiodothyronine, Dill, Dimethylglycine (DMG), Dimethylhexylamine (DMHA), Dimethylsulfoxide (DMSO), Diosmin, Divi-Divi, Docosahexaenoic Acid (DHA), Dodder, Dolomite, Dong Quai, Douglas fir, Dragon Fruit, Dragon's Blood, Duckweed, Dulse, Durabolin, Durian, Dusty Miller, Dwarf Elder, Dwarf Pine Needle, Dyer's Broom, Dymethazine, Eastern Hemlock, Eastern Red Cedar, Ecdysteroids, *Echinacea*, Ecklonia Cava, Eicosapentaenoic Acid (EPA), Elderberry, Elderflower, Elecampane, Elemi, Eleuthero, Ellagic Acid, Elm Bark, Emu Oil, English Adder's Tongue, English Horsemint, English Ivy, English Walnut, Ephedra, Epiandrosterone, Epistane, Equol, Ergot, Ergothioneine, Eryngo, *Eucalyptus, Euphorbia cyparissias, Euphorbia hirta*, European Barberry, European Buckthorn, European Chestnut, European Five-finger Grass, European Mandrake, European Mistletoe, Eurycoma *Longifolia*, Evening Primrose, Evodia, Eyebright, Fadogia *Agrestis*, False Unicorn, Fennel, Fenugreek, Fermented Milk, Fermented Wheat Germ Extract, Fever Bark, Feverfew, Ficin, Field Scabious, Fig, Figwort, Fir, Fireweed, Fish Oil, Flaxseed, Flaxseed Oil, Fluoride, Fly Agaric Mushroom, Fo-Ti, Folic Acid, Fool's Parsley, Forget-Me-Not, Forsythia, Foxglove, Frankincense, Fringetree, Frostwort, Fructo-Oligosaccharides (FOS), Fucus Vesiculosus, Fulvic Acid, Fumitory, G, Galacto-oligosaccharides (GOS), *Galbanum*, Galphimia *Glauca*, Gamboge, Gamma Butyrolactone (GBL), Gamma-Aminobutyric Acid (GABA), Gamma-Hydroxybutyrate (GHB), Gamma-Linolenic Acid (GLA), Gamma-oryzanol, Garcinia, Garden Cress, *Gardenia*, Garlic, Gelatin, *Gelsemium*, Genistein Combined Polysaccharide, Gentian, German Chamomile, German Ipecac, German Sarsaparilla, Germander, Germanium, Ginger, Ginkgo, Globe Flower, Globemallow, Glossy Privet, Glucomannan, Glucosamine, Glucuronolactone, Glutaurine, Glutamine, Glutathione, Glycerol, Glycine, Glycolic Acid, Glycomacropeptide, Glyconutrients, Goa Powder, Goat's Rue, Goji, Golden Ragwort, Goldenrod, Goldenseal, Goldthread, Gossypol, Gotu Kola, Goutweed, Grains of Paradise, Grape, Grapefruit, Gravel Root, Graviola, Great Plantain, Greater Burnet, Greater Celandine, Greek Sage, Green Coffee, Green Tea, Griffonia *Simplicifolia*, Ground Ivy, Ground Pine, Groundsel, Guaiac Wood, Guar Gum, Guarana, Guarumo, Guava, Guggul, Gum arabic, Gumweed, Gymnema, Halodrol-50, Haronga, Hartstongue, Hawaiian baby woodrose, Hawthorn, Hazelnut, Heart's Ease, Heather, Hedge Mustard, Hedge-Hyssop, Hemlock, Hemlock Water Dropwort, Hemp, Hemp Agrimony, Hempnettle, Henbane, Henna, Herb Paris, Herb Robert, Hercules Club, Hesperidin, Hexadrone, Hexylamine, *Hibiscus sabdariffa*, Higenamine, Histidine, Holly, Hollyhock, Holy Basil, Homotaurine, Honey, Honeysuckle, Hoodia, Hops, Hordenine, Horny Goat Weed, Horse Chestnut, Horsemint, Horseradish, Horsetail, Hound's Tongue, Houseleek, Hu Zhang, Humic Acid, Huperzine A, Hyacinth Bean, Hyaluronic Acid, *Hydrangea*, Hydrazine Sulfate, Hydroxymethylbutyrate (HMB), Hyperimmune Egg, Hyssop, Iboga, Iceland Moss, Idebenone, Ignatius Bean, Immortelle, Indian *Cassia*, Indian Gooseberry, Indian Long Pepper, Indian Snakeroot, Indigo pulchra, Indium, Indole-3-Carbinol, Inosine, Inositol, Inositol Nicotinate, Inulin, Iodine, IP-6, Ipecac, Iporuru, Ipriflavone, Iron, Irvingia *gabonensis*, Isatis, Isopropylnorsynephrine, Ivy Gourd, Jaborandi, Jackfruit, Jalap, Jamaican Dogwood, Jambolan, Japanese Apricot, Japanese Mint, Japanese Persimmon, Jasmine, Java Tea, Javanese Turmeric, Jenny Craig Diet, Jequirity, Jewelweed, Jiaogulan, Jimson Weed, Job's Tears, Jojoba, Juniper, Justicia pectoralis, K2/Spice, Kale, Kamala, Kaolin, Karaya Gum, Kava, Kefir, Ketogenic diet, Khat, Khella, Kinetin, Kiwi, Knotweed, Kohlrabi, Kombucha, Korean Pine, Kousso, Kratom, Krill Oil, Kudzu, L-Arginine, L-Carnitine, L-Citrulline, L-Cysteine, L-Ornithine-L-Aspartate, L-Tryptophan, Labdanum, *Laburnum*, Lactase, Lactic Acid, Lacticaseibacillus *casei, Lacticaseibacillus paracasei, Lacticaseibacillus rhamnosus, Lactiplantibacillus pentosus, Lactiplantibacillus plantarum, Lactobacillus acidophilus, Lactobacillus crispatus, Lactobacillus delbrueckii, Lactobacillus gasseri, Lactobacillus helveticus, Lactobacillus jensenii, Lactobacillus johnsonii*, Lactoferrin, Lady's Bedstraw, *Laminaria*, Larch Arabinogalactan, Larch Turpentine, *Lathyrus*, Latilactobacillus sakei, Laurelwood, Lauric Acid, Lavender, Lavender Cotton, Laxogenin, Lecithin, Lemon, Lemon Balm, Lemon *Eucalyptus*, Lemon *Verbena*, Lemongrass, Lentinan, Lesser Celandine, Levant Berry, Levilactobacillus *brevis*, Licorice, Ligandrol, Ligilactobacillus *salivarius*, Lily-of-the-Valley, Lime, Limonene, Limosilactobacillus *fermentum, Limosilactobacillus reuteri*, Linden, Lingonberry, Lion's Mane Mushroom, Lipase, Lithium, Liver Extract, Liverwort, *Lobelia*, Logwood, Lorenzo's Oil, Lotus, Lousewort, Lovage, Luffa, Lunasin, Lungmoss, Lungwort, Lupin, Lutein, Lychee, Lycopene, Lysine, M1-4ADD, Maca, Macadamia Nut, Mace, Madagascar Periwinkle, Madder, Magnesium, *Magnolia*, Maidenhair Fern, Maitake Mushroom, Malabar Nut, Male Fern, Malic Acid, Mallow, Manaca, Manchurian Thorn, Manganese, Mangosteen, Manna, Maqui, Maral Root, Maritime Pine, Marjoram, Marsh Blazing Star, Marsh Labrador Tea, Marsh Marigold, Marshmallow, Masterwort, Mastic, Meadowsweet, Medium Chain Triglycerides (MCTs), Melanotan, Melatonin, Mentabolan, Mercury Herb, Mesoglycan, Methasterone, Methionine, Methoxydienone, Methoxylated Flavones, Methyldiazinol, Methylstenbolone, Methylsulfonylmethane (MSM), Methylsynephrine, Mezereon, Milk Thistle, Miracle Fruit, Molybdenum, Moneywort, Monolaurin, Monterey Pine, Moringa, Mormon Tea, Motherwort, Mountain Ash, Mountain Flax, Mountain Laurel, Mouse-Ear Hawkweed, Mugwort, Muira Puama, Mullein, Musk, Myrcia, Myrrh, Myrtle, N, N-DMPEA, N-Acetyl Cysteine (NAC), N-Methyltyramine, NADH, Nasturtium, Nattokinase, Neem, Nerve Root, New Jersey Tea, New Zealand Green-Lipped Mussel, Niacin, Niacinamide, Niauli oil, Nickel, Nicotinamide Riboside, Nikko Maple, Noni, Northern Prickly Ash, Norway Spruce, Nutmeg, Nux Vomica, Oak Moss, Oats, Octacosanol, Octopamine, *Oleander*, Oleic Acid, Olive, Olive Oil, Omega-6 Fatty Acids, Onion, Oolong Tea, Orchic extract, Oregano, Oregon Grape, Oriental Arborvitae, Ornamental Marigold, Ornithine, Ornithine Ketoglutarate (OKG), Orris, Oscillococcinum, Osha, Ostarine, Ostrich Fern, Oswego Tea, Ox-Eye Daisy, Padang *Cassia*, Pagoda Tree, Palm Oil, Palmitoylethanolamide (PEA), *Panax Ginseng, Panax Notoginseng*, Pancreatic Enzyme Products, Pangamic Acid, Pantethine, Pantothenic Acid, Pao Pereira, Papain, *Papaya*, Para-Aminobenzoic Acid (PABA), Pareira, Parsley, Parsley Piert, Parsnip, Partridgeberry, Passion Flower, Pata De Vaca, Patchouli Oil, Pau D'Arco, Pea Protein, Peanut Oil, Pear, Pectin, Pedunculate Oak, Pellitory, Pellitory-of-the-Wall, Pennyroyal, Peony, Peppermint, *Perilla*, Perillyl Alcohol, Periwinkle, Peru Balsam, Peyote, *Phaseolus Vulgaris*, Pheasant's Eye, Phellodendron, Phenethylamine (PEA), Phenibut, Phenpromethamine, Phenylalanine, Phlorizin, Phosphate Salts, Phosphatidylcholine, Phosphatidylserine, Phytase, Picamilon, Picrorhiza, Pimpinella, Pinellia Ternata, Pink Root, Pipsissewa, Piracetam, Pitcher Plant, Plant Sterols, Pleurisy root, Plum, *Podophyllum*, Poinsettia, Poison Ivy, Pokeweed, Polarity Therapy, Policosanol, Polydextrose, Polypodium Leucotomos, Pomegranate, Poplar, Poppy Seed, Poria Mushroom, Potassium, Potato, Potentilla, Pregnenolone, Premorse, Prickly Pear Cactus, Procaine, Progesterone, Proline, Propionyl-L-Carnitine, Propolis, Proteolytic Enzymes (Proteases), Psilocybin, Pu-erh Tea, *Pulsatilla*, Pumpkin, Purple Loosestrife, Purple Nut Sedge, Pygeum, Pyrethrum, Pyruvate, Quassia, Quebracho Blanco, Queen's Delight, Quercetin, *Quillaia, Quince, Quinoa*, Rabdosia *Rubescens*, Radish, Raspberry Ketone, Rauvolfia Vomitoria, Rauwolscine, Red Clover, Red Maple, Red Raspberry, Red Sandalwood, Red Soapwort, Red Yeast Rice, Red-spur Valerian, Reed Herb, Rehmannia, Reishi Mushroom, Resveratrol, Rhatany, *Rhodiola*, Rhubarb, Riboflavin, Ribose, Rice Bran, Rice Bran Arabinoxylan Compound, Rice protein, RNA and DNA, Rock Rose, Roman Chamomile, Rooibos, Rose Geranium Oil, Rose Hip, Rosemary, Royal Jelly, Rue, Rupturewort, Rusty-leaved *Rhododendron*, Rutin, Rye Grass, S-23, *Saccharomyces Boulardii*, Safed Musli, Safflower, Saffron, Sage, Saigon Cinnamon, Salacia, Salatrim, Salep, *Salvia* divinorum, SAMe, Samphire, Sandy Everlasting, Sangre de Grado, Sanicle, Sarsaparilla, *Sassafras*, Savin Tops, Saw Palmetto, Scarlet Pimpernel, Sceletium, Schisandra, Schizonepeta, Scopolia, Scotch Broom, Scotch Thistle, Scurvy Grass, Sea Buckthorn, Sea Moss, Secretin, Securinega *Suffruticosa*, Selenium, Self-Heal, Senega, *Senna*, Serine, Serrapeptase, Sesame, Sessile Oak, Shark Cartilage, Shark Liver Oil, Shea Butter, Shellac, Shepherd's Purse, Shiitake Mushroom, Siberian Cocklebur, *Sida Cordifolia*, Silicon, Simaruba, Sitostanol, Skullcap, Skunk Cabbage, Slippery Elm, Smartweed, Smooth Alder, Snake Skin, Sodium, Sodium Bicarbonate, Sodium Tetrachloroaurate, Solomon's Seal, Sorghum, Sorrel, Soy, Soybean Oil, Spanish Broom, Spanish *Origanum* Oil, Spearmint, Spinach, Spiny Restharrow, Spleen extract, Spotted Geranium, Squalamine, Squill, St. John's Wort, Star Anise, Star of Bethlehem, Stavesacre, Stenabolic, Stereosp ermum, *Stevia*, Stinging Nettle, Stone Root, Storax, Strawberry, *Streptococcus thermophilus*, Strontium, Strophanthus, Succinate, Sulbutiamine, Sulforaphane, Sulfur, Suma, Sumbul, Summer Savory, Sundew, Sunflower Oil, Superoxide Dismutase (SOD), Swallowroot, Swamp Milkweed, Sweet Almond, Sweet Annie, Sweet Cherry, Sweet Cicely, Sweet Clover, Sweet Gale, Sweet Orange, Sweet Sumac, Sweet Vernal Grass, Sweet Violet, Sweet Woodruff, Syrian Rue, Tamarind, *Tamarix Dioica*, Tangerine, Tannic acid, Tansy, Tansy Ragwort, Tapioca, Tarragon, Tart Cherry, Tartaric Acid, Taurine, Tea Tree Oil, Teazle, Terminalia, Testolone, Tetrahydrocannabivarin (THCV), Theacrine, Theaflavin, Theanine, Thiamine, Threonine, *Thuja*, Thunder God Vine, Thyme, Thymus extract, Thyroid Extract, Tianeptine, Timothy Grass, Tin, Tinospora *Cordifolia*, Tiratricol, Tocotrienols, Tolu Balsam, Tomato, Tonka Bean, Toothed Clubmoss, Tormentil, Tragacanth, Trailing Arbutus, Transfer Factor, Traveler's Joy, Tree of Heaven, Tree Tobacco, Tree Turmeric, Trendione, Tribulus, *Trichopus* Zeylanicus, Tronadora, Trypsin, Tung Seed, Turkey Corn, Turkey Tail Mushroom, Turmeric, Turpentine Oil, Turtlehead, Tylophora, Tyramine, Tyrosine, Ubiquinone, Umckaloabo, Usnea, Uva *Ursi*, Uzara, Valerian, Vanadium, Vanilla, *Verbena, Veronica*, Vetiver, Vietnamese Coriander, Vinpocetine, Vitamin A, Vitamin B1, Vitamin B2, Vitamin B12, Vitamin B6, Vitamin C, Vitamin D, Vitamin E, Vitamin K, Vitamin O, Wafer Ash, Wahoo, Wallflower, Wasabi, Water Avens, Water Dock, Water Hemlock, Watercress, Wheat Bran, Wheatgrass, Whey Protein, White Dead Nettle Flower, White Hellebore, White Horehound, White Lily, White Mulberry, White Mustard, White Oak, White Pepper, White Sandalwood, Wild Carrot, Wild Cherry, Wild Daisy, Wild Indigo, Wild Lettuce, Wild Mint, Wild Thyme, Wild Yam, Willard Water, Willow Bark, Wine, Winter Cherry, Winter Savory, Wintergreen, Witch Hazel, Wood Anemone, Wood Sage, Wood Sorrel, Wormseed, Wormwood, Xanthan Gum, Xanthoparmelia, Xylitol, Yarrow, Yellow Dock, Yellow Loosestrife, Yellow Toadflax, Yerba Mansa, Yerba Mate, Yerba Santa, Yew, Yin Chen, Ylang Ylang Oil, Yogurt, Yohimbe, *Yucca*, Zeaxanthin, Zedoary, Zinc, Zizyphus, carnitine or a salt, ester, or amide suitable for human ingestion thereof, acetyl-L-carnitine or a salt, ester, or amide suitable for human ingestion thereof, propionyl-L-carnitine or a salt, ester, or amide suitable for human ingestion thereof, alpha lipoic acid, alpha-GPC, aniracetam, piracetam, phenylpiracetam, apoaequorin, artichoke, ashwagandha, astaxanthin, Bacopa monnieri, cat's claw, catuaba, cannabidiol (CBD), Celastris paniculatus, centrophenoxine, citicoline, Clitoria ternatea, coluracetam, *Convolvulus* pluricaulis, ubiquinone (for example, Coenzyme Q10), creatine or a salt, ester, or amide suitable for human ingestion thereof, choline or a salt, ester, or amide suitable for human ingestion thereof, docosahexaenoic acid (DHA), dimethylethanolamine (DMAE), forskolin, *Ginkgo biloba, ginseng*, gotu kola, guarana, kanna, kava kava, kratom, L-glutamine or a salt, ester, or amide suitable for human ingestion thereof, L-phenylalanine or a salt, ester, or amide suitable for human ingestion thereof, L-theanine or a salt, ester, or amide suitable for human ingestion thereof, L-tryptophan or a salt, ester, or amide suitable for human ingestion thereof, lecithin or a salt, ester, or amide suitable for human ingestion thereof, lemon balm, lion's mane mushroom, *magnolia*, medium chain triglycerides, reduced nicotinamide adenine dinucleotide (NADH), nefiracetam, nicotine, arecoline, noopept, oatstraw, oxiracetam, passion flower, phenibut, phosphatidylcholine, phosphatidylserine, picamilon, pine bark extract, pramiracetam, pyrroloquinoline quinone (PQQ), pterostilbene, resveratrol, rosemary, *Rhodiola rosea*, S-adenosyl methionine (SAMe), schizandrol-A, St. John's wort, sulbutiamine, taurine or a salt, ester, or amide suitable for human ingestion thereof, turmeric, L-tyrosine or a salt, ester, or amide suitable for human ingestion thereof, N-acetyl-L-tyrosine or a salt, ester, or amide suitable for human ingestion thereof, uridine, valerian, vinpocetine, thiamine or a salt, ester, or amide a salt, ester, or amide suitable for human ingestion thereof, niacin or a salt, ester, or amide suitable for human ingestion thereof, pantothenic acid or a salt, ester, or amide suitable for human ingestion thereof, vitamin B6 or a salt, ester, or amide suitable for human ingestion thereof, vitamin B8 or a salt, ester, or amide suitable for human ingestion thereof, vitamin B9 or a salt, ester, or amide suitable for human ingestion thereof, vitamin B12 or a salt, ester, or amide suitable for human ingestion thereof, and yerba mate.

Compositions and/or formulations of the present disclosure may be administered in any form, including a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof for example. Compositions and/or formulations of the present disclosure may also include an acceptable additive (e.g., one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or an acceptable carrier (e.g., one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

Implementations of the ammonium phenoxide of curcumin or curcuminoid may conveniently be presented in unit dosage form. Unit dosage formulations may be those containing a daily dose or unit, a daily sub-dose, or an appropriate fraction thereof, of the administered components as described herein.

A dosage unit may include the ammonium phenoxide of curcumin or curcuminoid and at least one dissolution enhancer for example, such as sodium carbonate, potassium carbonate, magnesium carbonate, calcium carbonate, zinc carbonate, copper carbonate and iron carbonate, sodium bicarbonate, potassium bicarbonate, magnesium bicarbonate, calcium bicarbonate, zinc bicarbonate, copper bicarbonate and/or iron bicarbonate. In addition, a dosage unit may include the ammonium phenoxide of curcumin or curcuminoid admixed with pharmaceutically acceptable additives.

The dosage for oral use of the ammonium phenoxide of curcumin or curcuminoid can be from 1 to 30,000 mg per day, split into one or more dosages. For exercise performance enhancing purposes, the formulation is administered (for example, by ingestion) prior to exercise, for example any time between 3 days prior to exercise and right before exercise. In certain implementations, the formulation is administered one hour before exercise.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

It should be appreciated that any of the components of particular implementations of the ammonium phenoxide of curcumin or curcuminoid may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion compoundation, lyophilization, melting, mixed, molding, pan coating, solvent dehydration, sonication, spheronization, spray chilling, spray congealing, spray drying, and/or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Those of ordinary skill in the art will be able to readily select manufacturing equipment and pharmaceutically acceptable additives or inert ingredients to manufacture implementations of the ammonium phenoxide of curcumin or curcuminoid. For the exemplary purposes of this disclosure, some examples of pharmaceutically acceptable additives or inert ingredients and manufacturing process are included below, particularly those that relate to manufacture of implementations of the ammonium phenoxide of curcumin or curcuminoid in tablet form. Notwithstanding the specific examples given, it will be understood that those of ordinary skill in the art will readily appreciate how to manufacture implementations of the ammonium phenoxide of curcumin or curcuminoid according to the other methods of administration and delivery disclosed in this document.

A particular implementation of the ammonium phenoxide of curcumin or curcuminoid may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of the ammonium phenoxide of curcumin or curcuminoid may also include a binder. Binders are any agents used to impart cohesive qualities to powdered material through particle-particle bonding. Binders may include, for example, matrix binders (e.g., dry starch, dry sugars), film binders (e.g., celluloses, bentonite, sucrose), and chemical binders (e.g., polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of the ammonium phenoxide of curcumin or curcuminoid to facilitate the breakup or disintegration of tablets after administration. Disintegrators may include, for example, starch, starch derivatives, clays (e.g., bentonite), algins, gums (e.g., guar gum), cellulose, cellulose derivatives (e.g., methyl cellulose, carboxymethyl cellulose), croscarmellose sodium, croscarmellose cellulose, and other organic and inorganic materials.

Implementations of the ammonium phenoxide of curcumin or curcuminoid may include diluents, or any inert substances added to increase the bulk of the curcumin-ammonium phenoxide to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in an curcumin-ammonium phenoxide and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

Implementations of the ammonium phenoxide of curcumin or curcuminoid may also be administered through use of amphipathic lipid delivery systems (such as liposomes and unilamellar vesicles), caplet systems, oral liquid systems, parenteral and/or intravenous systems, topical systems (creams, gels, transdermal patches, etc.), intranasal systems, rectal or vaginal systems, and many other delivery methods and/or systems known to those of ordinary skill in the art.

Those of ordinary skill in the art will readily be able to select additional pharmaceutically acceptable additives to enable delivery of implementations of a pharmaceutical composition from the disclosure in this document.

With respect to delivery of particular implementations of the ammonium phenoxide of curcumin or curcuminoid, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be, for example, round, oval, oblong, cylindrical, rectangular, or triangular. The tablets may be optionally scored so that they may be separated into different dosages. They may differ greatly in size and weight depending on the amount of the pharmaceutically acceptable active agent or agents present and the intended route of administration. They are divided into two general classes: compressed tablets and molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be affected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of the ammonium phenoxide of curcumin or curcuminoid have been described in particular sequences of steps and/or in particular forms in the examples, it will be understood that such manufacture is not limited to the specific order of steps or forms as disclosed. For example, a different solvent than water in which ammonia and curcumin is readily soluble and which can be evaporated can be used. Any steps or sequences of steps of manufacture of implementations of the ammonium phenoxide of curcumin or curcuminoid in any form are given as examples of possible steps or sequences of steps or potential forms and not as limitations, since many possible manufacturing processes and sequences of steps may be used to manufacture curcumin-ammonium phenoxide implementations in a wide variety of forms.

In other aspects, the disclosure relates to methods of treating a curcumin-improvable condition in a subject. The method may include administering a curcumin ammonium phenoxide or an ammonium phenoxide of curcumin metabolites to a subject. Thus, use of curcumin ammonium phenoxide or an ammonium phenoxide of curcumin metabolites for the treatment of a curcumin-improvable condition is disclosed. In some aspects, the use of curcumin ammonium phenoxide or an ammonium phenoxide of curcumin metabolites for the manufacture of medicament, therapeutic composition, or nutraceutical composition is disclosed.

In some aspects, the methods and uses disclosed herein include reducing inflammation in a human subject, reducing lactate production during or after exercise in a human subject, increasing endurance in a human subject, increasing strength in a human subject, reducing total cholesterol in a subject, reducing LDL cholesterol in a subject, treating depression in a subject, treating allergic rhinitis in a subject, reducing triglycerides in a subject, treating hyperlipidemia in a subject, treating non-alcoholic fatty liver disease in a subject, treating alcoholic fatty liver disease in a subject, treating oral mucositis in a subject, treating osteoarthritis in a subject, treating pruritus in a subject, treating Alzheimer's disease in a subject, treating peptic ulcers in a subject, treating acne in a subject, treating age-related cognitive decline in a subject, treating amenorrhea in a subject, treating ankylosing spondylitis in a subject, treating asthma in a subject, increasing athletic performance in a subject, treating benign prostatic hyperplasia in a subject, treating beta-thalassemia in a subject, treating and enhancing healing of bruises in a subject, treating cachexia in a subject, treating canker sores in a subject, treating chemotherapy-induced acral erythema in a subject, treating chemotherapy-induced constipation in a subject, treating chemotherapy-induced diarrhea in a subject, treating chemotherapy-induced nausea and vomiting (CINV) in a subject, treating chemotherapy-induced peripheral neuropathy in a subject, treating chronic kidney disease (CKD) in a subject, treating colorectal adenoma in a subject, treating colorectal cancer in a subject, decreasing the risk of cardiac injury after coronary artery bypass graft (CABG) surgery, reducing symptoms of COVID-19 in a subject, treating Crohn's disease in a subject, treating denture stomatitis in a subject, treating diabetes in a subject, treating diabetic foot ulcers in a subject, treating diabetic nephropathy in a subject, treating dysmenorrhea in a subject, treating dyspepsia in a subject, treating erythema in a subject, treating exercise-induced muscle soreness in a subject, treating gingivitis in a subject, treating gout in a subject, treating *Helicobacter pylori* in a subject, treating impaired glucose tolerance (prediabetes) in a subject, treating irritable bowel syndrome (IBS) in a subject, treating joint pain in a subject, treating juvenile idiopathic arthritis (JIA) in a subject, treating knee pain in a subject, treating lichen planus in a subject, treating metabolic syndrome in a subject, treating migraine headache in a subject, reducing myocardial injury after myocardial infarction (MI) in a subject, treating obesity in a subject, reducing body fat percentage in a subject, increasing body mass index in a subject, treating oral submucous fibrosis in a subject, treating acute pain in a subject, treating periodontitis in a subject, treating polycystic ovary syndrome (PCOS) in a subject, treating postoperative pain in a subject, treating premenstrual syndrome (PMS) in a subject, treating prostate cancer, treating psoriasis in a subject, improving quality of life for chronic ailments in a subject, treating radiation dermatitis in a subject, treating radiation proctopathy in a subject, treating respiratory tract infection in a subject, treating rheumatoid arthritis (RA) in a subject, treating sarcopenia in a subject, treating schizophrenia in a subject, treating sepsis in a subject, treating stress in a subject, treating systemic lupus erythematosus (SLE) in a subject, treating tuberculosis in a subject, treating ulcerative colitis in a subject, treating uveitis in a subject, and/or improving wound healing in a subject. For simplicity, the aforementioned uses are referred to herein as "curcumin-improvable conditions".

Implementations of the ammonium phenoxide of curcumin or curcuminoid are particularly useful in increasing athletic performance and alleviating various ailments as discussed above. For all of the above curcumin-improvable conditions, the curcumin complexes with ammonia and related formulations described herein provide the beneficial effects of curcumin at a lower dose of curcumin than administering curcumin alone. In other aspects, the curcumin complexes with ammonia and related formulations at a higher degree than a comparable dose of curcumin.

The symptoms and etiology of curcumin-improvable conditions that can be ameliorated by administration of curcumin and the formulations described herein are described in "Handbook of Diseases", 3rd Edition by Springhouse Corporation, which is fully incorporated by reference herein. Furthermore, the contents of all references, patents, and published patent applications cited throughout this application, if any, are incorporated herein by reference in their entirety for all purposes.

EXAMPLES

The present disclosure is further illustrated by the following examples that should not be construed as limiting.

Example 1

At room temperature, 95% curcumin powder (2.68 mol or 987.26 g curcumin) was dissolved slowly while stirring in a glass beaker containing 1000 ml of 10% ammonia solution (5.36 molarity, 91.12 g ammonia). The mixture was left to dry at 60° C. under vacuum. The resulting product (ammonium phenoxide of curcumin) was then grinded. The powder was then mixed at a 2:1 ratio with sodium carbonate.

Figure 5:
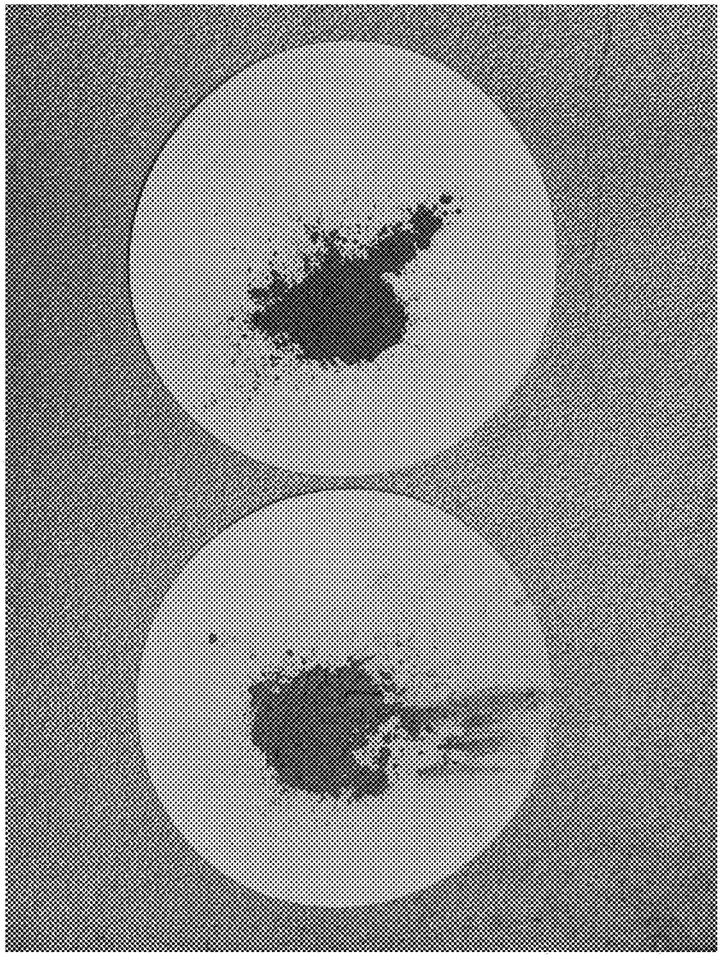
FIG. 5 is a photograph of the ammonium phenoxide of curcumin (top) and curcumin (bottom).
Figure 6:
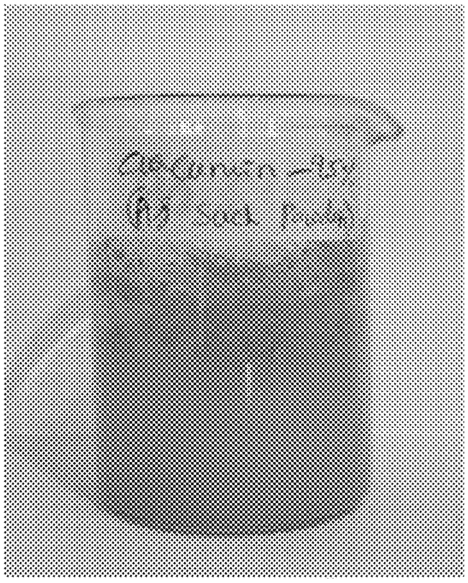
FIG. 6 is a photograph of a beaker containing 50 ml water and 0.5. g curcumin.
Figure 7:
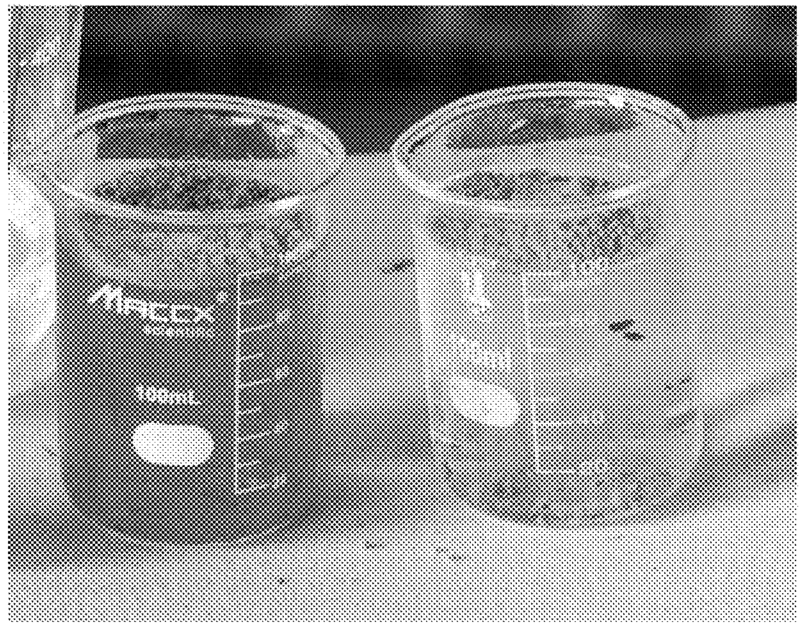
FIG. 7 is a photograph of two beakers taken at about one minute after 1 g 95% curcumin powder (right) or 1 g ammonium phenoxide of curcumin (left) is added to 100 ml water. The mixture was not stirred.
Figure 8:
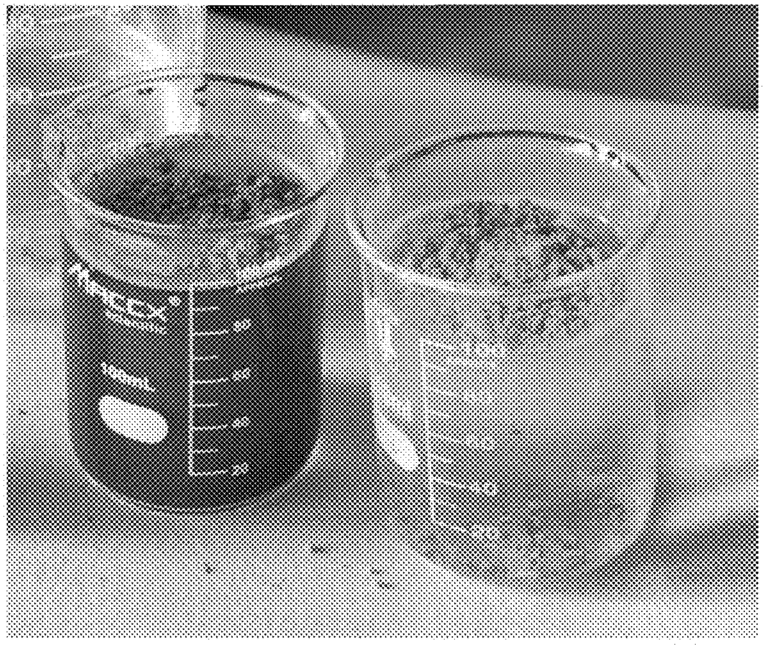
FIG. 8 is a photograph of two beakers taken at about ten minutes after 1 g 95% curcumin powder (right) or 1 g ammonium phenoxide of curcumin (left) is added to 100 ml water. The mixture was not stirred.
Figure 9:
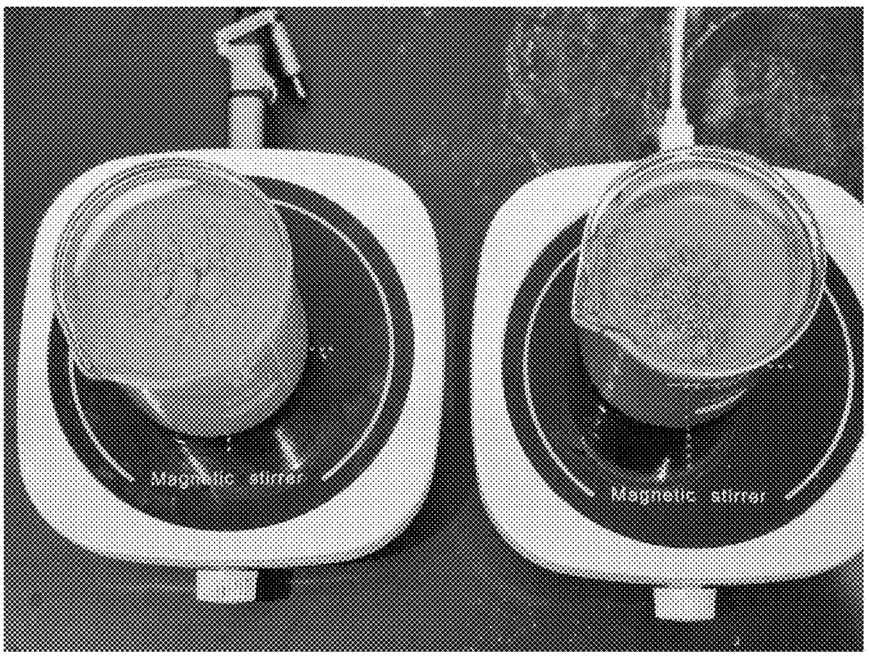
FIG. 9 is a photograph of two beakers taken at about 10 seconds after 1 g 95% curcumin powder (left) or 1 g ammonium phenoxide of curcumin (right) is added to 100 ml water with stirring (1200 rpm with magnetic stirrer).
Figure 10:
FIG. 10 is a photograph of the filtrate of the solution of 1 g 95% curcumin in 100 ml water from FIG. 9 after the solution was centrifuged at 1000 rpm for 10 seconds.
Figure 11:
FIG. 11 is a photograph of the filtrate of the solution of 1 g ammonium phenoxide of curcumin in 100 ml water from FIG. 9 after the solution was centrifuged at 1000 rpm for 10 seconds.

As shown in FIG. 5, which compares the visible appearance of the ammonium phenoxide of curcumin (top) to that of regular curcumin, the phenoxide is noticeably darker in color. FIG. 6 shows the low solubility of curcumin in water. On the other hand, FIGS. 7 and 8 show that ammonium phenoxide of curcumin is a lot more water-soluble. Even without stirring, dissolution of the ammonium phenoxide of curcumin in water was visible at one minute after combining 1 g ammonium phenoxide of curcumin and 100 ml water without any stirring (FIG. 7). On the other than, even 10 minutes after combining 95% curcumin powder with water, there were no visible sign of curcumin dissolving in water. With stirring (at 1200 rpm with a magnetic stirrer), it took less than 10 seconds for all 1 gram of the ammonium phenoxide of curcumin to be dissolved in 100 ml of water (FIG. 9). As shown in FIG. 10, the solution containing 1 g 95% curcumin powder in 100 ml water resulted in no solubility even with stirring. After the solution was centrifuged at 1000 rpm for 10 seconds and then passed through filter, all of the curcumin powder was left on the filter paper while the filtrate was clear and lacked color. On the other hand, the filtrate produced from centrifuging the solution of 1 g ammonium phenoxide of curcumin in 100 ml water is the color of curcumin and no solid matter was left on the filter paper (FIG. 11).

Example 2

A 60-year-old male with chronic knee and shoulder pain used curcumin products at doses of 1-4 grams per day with no effect on his pain levels, including a curcumin product with piperine from a leading curcumin brand that supposedly caused curcumin to become more bioavailable at a dose of 2 grams 95% curcuminoids per day. Once the subject started ingesting the ammonium phenoxide of curcumin at a dose 1 gram twice per day, he started noticing improvement in his symptoms on the second day. He continued showing improvement in pain reduction during the next 30 days that he took the new formulation.

Example 3

A 42-year-old male subject who regularly trains ingested the ammonium phenoxide of curcumin at a dose of 1 gram in the morning and 1 gram at night the day before training. On training day, he ingested the ammonium phenoxide of curcumin 1 hour before commencing the training. The subject experienced longer time to exhaustion on the treadmill (Ifit treadmill, setting at 0 elevation and speed of 5 miles per hour): his time to exhaustion increased from 13 minutes to 15.5 minutes. For the arm curls test (maximum number of bicep curl repetitions performed in 30 seconds with appropriate weight) using a 40 lb dumbbell, the number of repetitions increased from 11 to 14. The day after training, his soreness was noticeably lower. Also, he recovered from exercise at nearly half the usual rate (1 day versus 2 days measured by muscle soreness and discomfort).

After a 3-day washout period (curcumin's half-life is ~7 hours), he took 1 gram of 95% curcumin extract on the night before another training day and another gram 1 hour before training. His time to exhaustion on the treadmill was 13 minutes. The maximum number of bicep curl repetitions performed in 30 seconds with the 40 lb dumbbell was 11 repetitions. His time to recovery (measured by muscle soreness and discomfort) was 2 days after training. Thus, regular curcumin had no effect on his exercise capacity and recovery, while the ammonium phenoxide of curcumin increased his exercise capacity and reduced the needed time for recovery.

The beneficial effect of the ammonium phenoxide of curcumin on exercise performance surprising, since ammonium has long been established to be related to fatigue and is regarded as a metabolic toxin that contributes to the development of fatigue. See Mutch and Banister, *Ammonia metabolism in exercise and fatigue: a review*, Med Sci Sports Exerc., 1983, 15 (1): 41-50. Specifically, ammonia production was observed from stimulated nerve, and it was found that the immediate source of ammonia from muscle appears to be a result of the deamination of AMP and is more apparent in fast-twitch than in slow-twitch fibers. Increases in blood ammonia levels have also been reported in rats after swimming and in humans after arm work, maximal cycle ergometry, and treadmill exercise. Elevated blood ammonia has also been linked to a surprising variety of functional and metabolic neurological disturbances other than exercise and fatigue, including the development of hepatic coma, convulsions from ammonia toxicity precipitated by high-pressure oxygen breathing, epileptic seizures, and decreased neuronal excitability. In addition, a number of genetic disorders with neural disability are characterized by elevated blood ammonia concentrations. Thus, the fact that the ammonium phenoxide of curcumin could enhance endurance and shorten recovery time while curcumin could not is a surprising effect of the described soluble form of curcumin.

Example 4

Figure 12:
FIG. 12 is a photograph of the filtrate of the solution of 2 g ammonium phenoxide of curcumin in 200 ml saturated citric acid solution (pH=3).
Figure 13:
FIG. 13 is a photograph of the filtrate of the solution of 2 g 95% curcumin in 200 ml saturated citric acid solution (pH=3).
Figure 14:
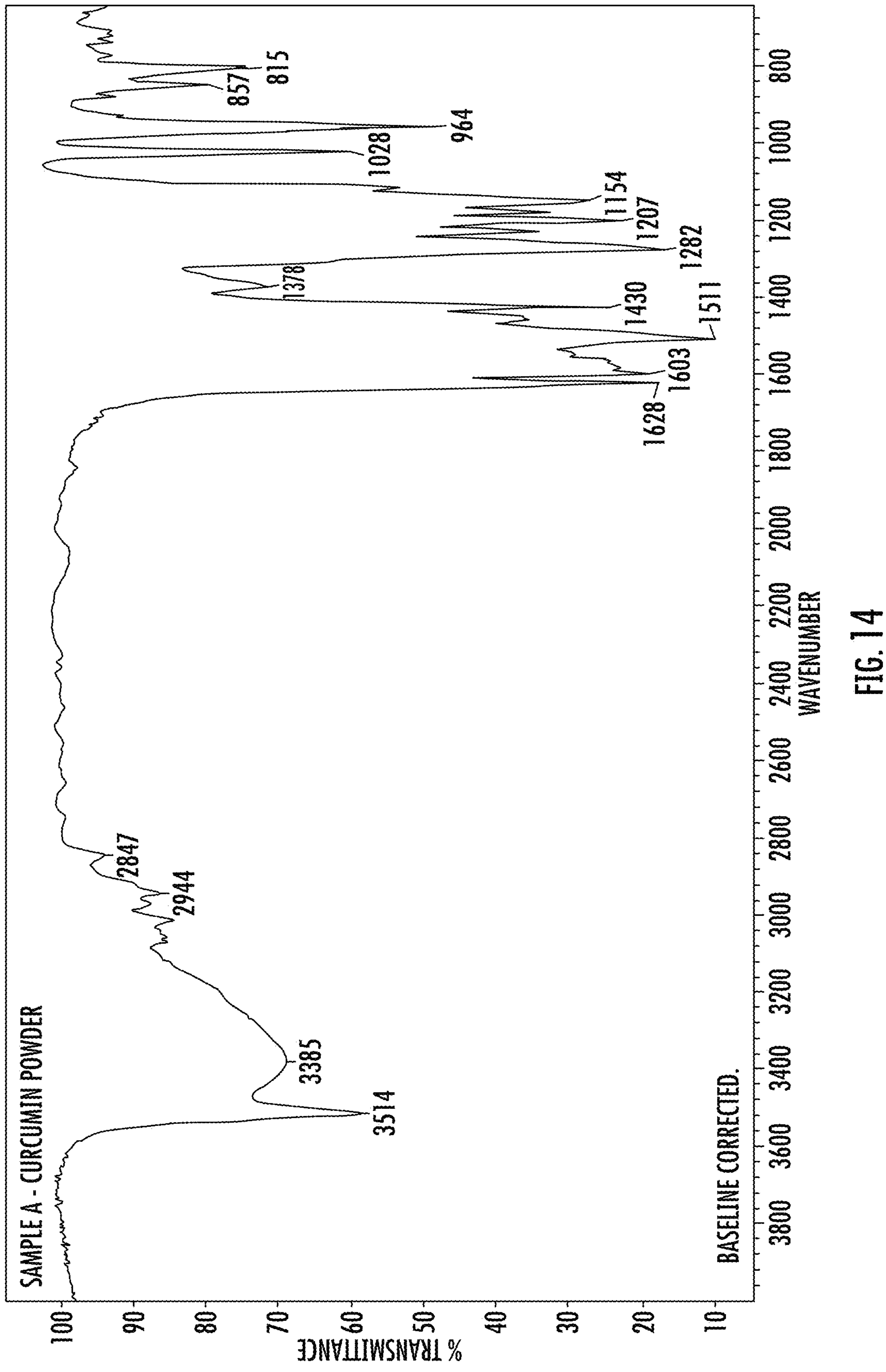
FIG. 14 is a spectra of curcumin powder using Fourier Transform Infrared Spectroscopy (FTIR).
Figure 15:
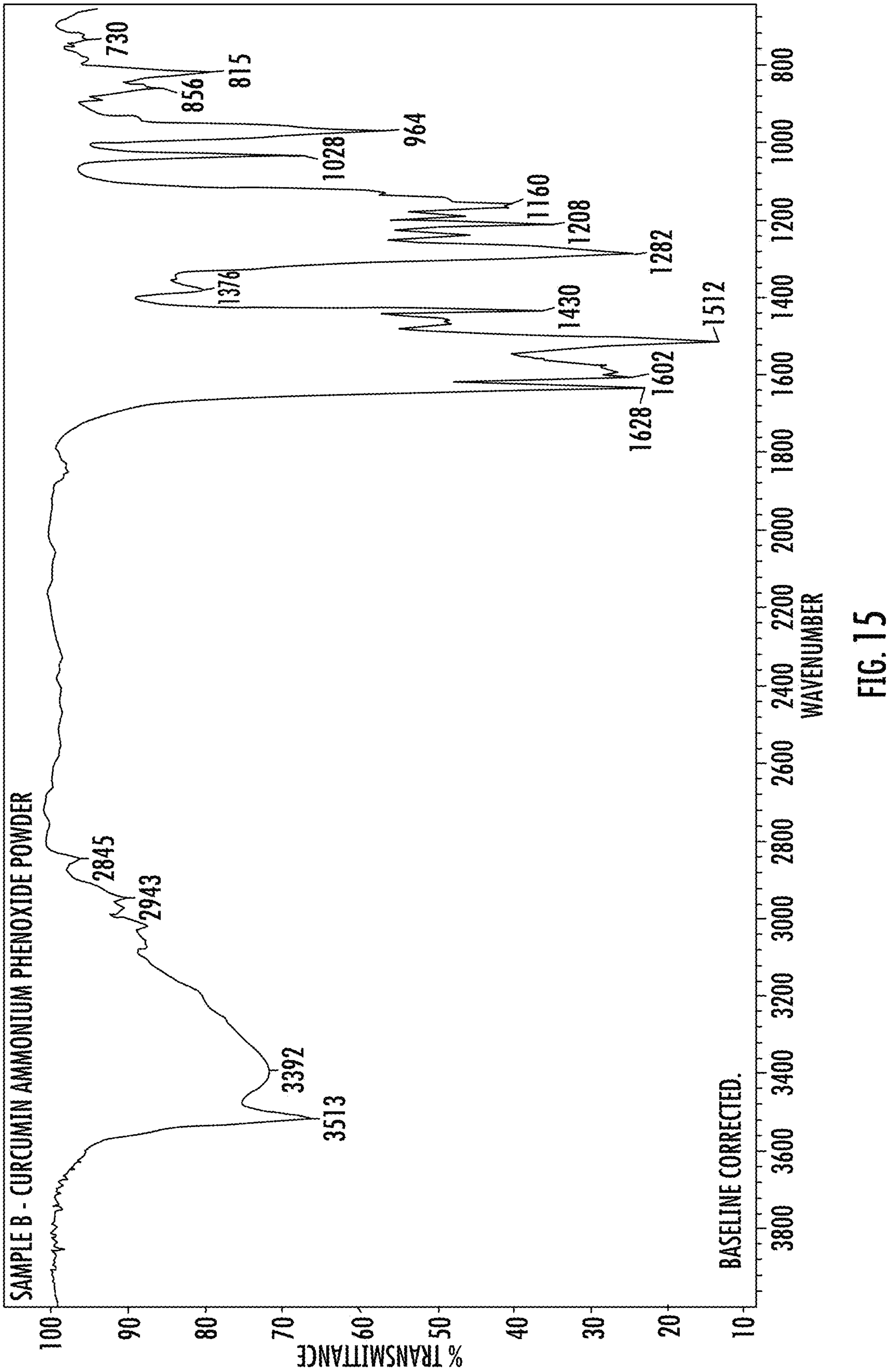
FIG. 15 is a spectra of the ammonium phenoxide of curcumin using FTIR.
Figure 16:
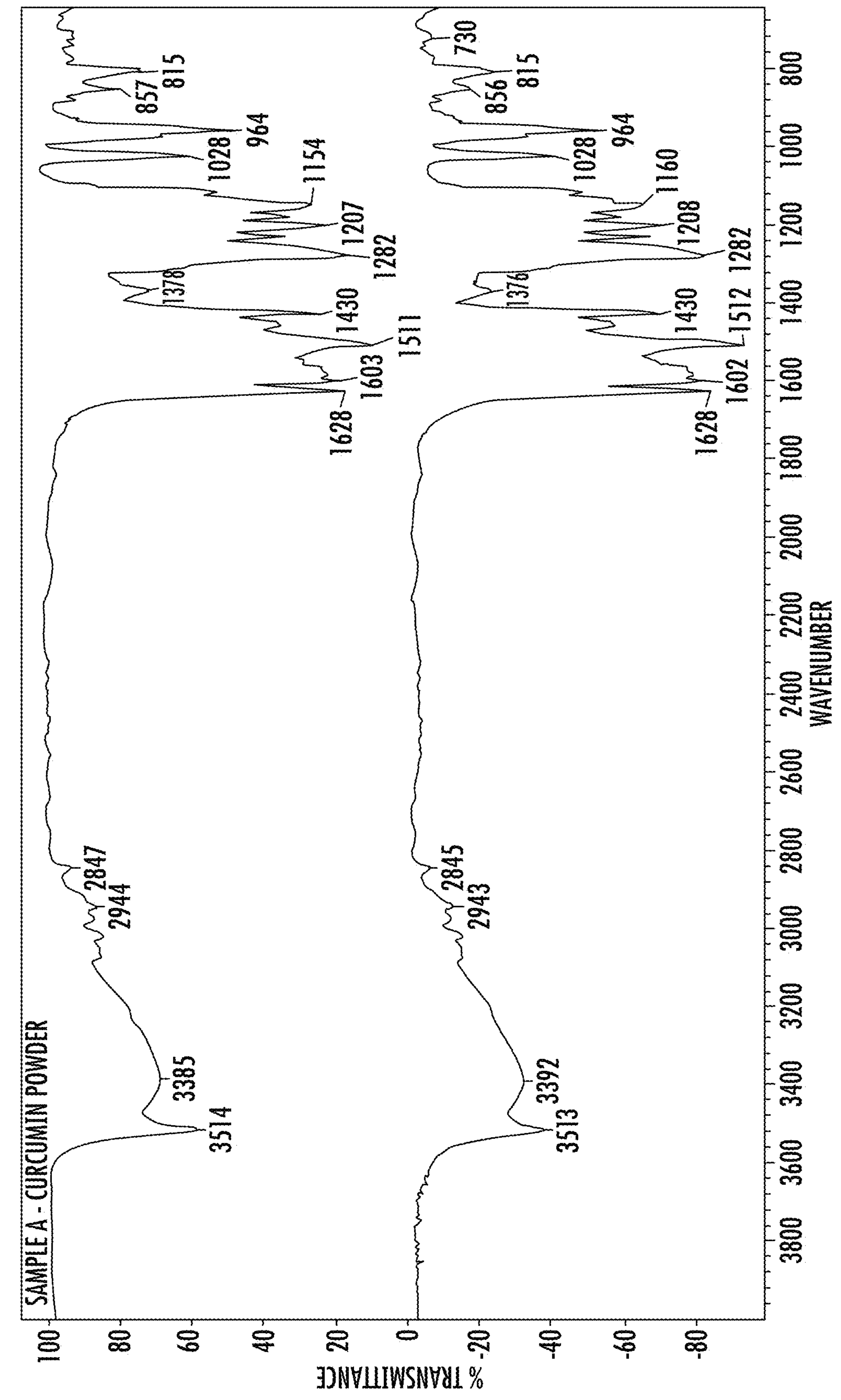
FIG. 16 depicts a plot of the curcumin spectra from FIG. 14 over the ammonium phenoxide of curcumin spectra from FIG. 15.
Figure 17:
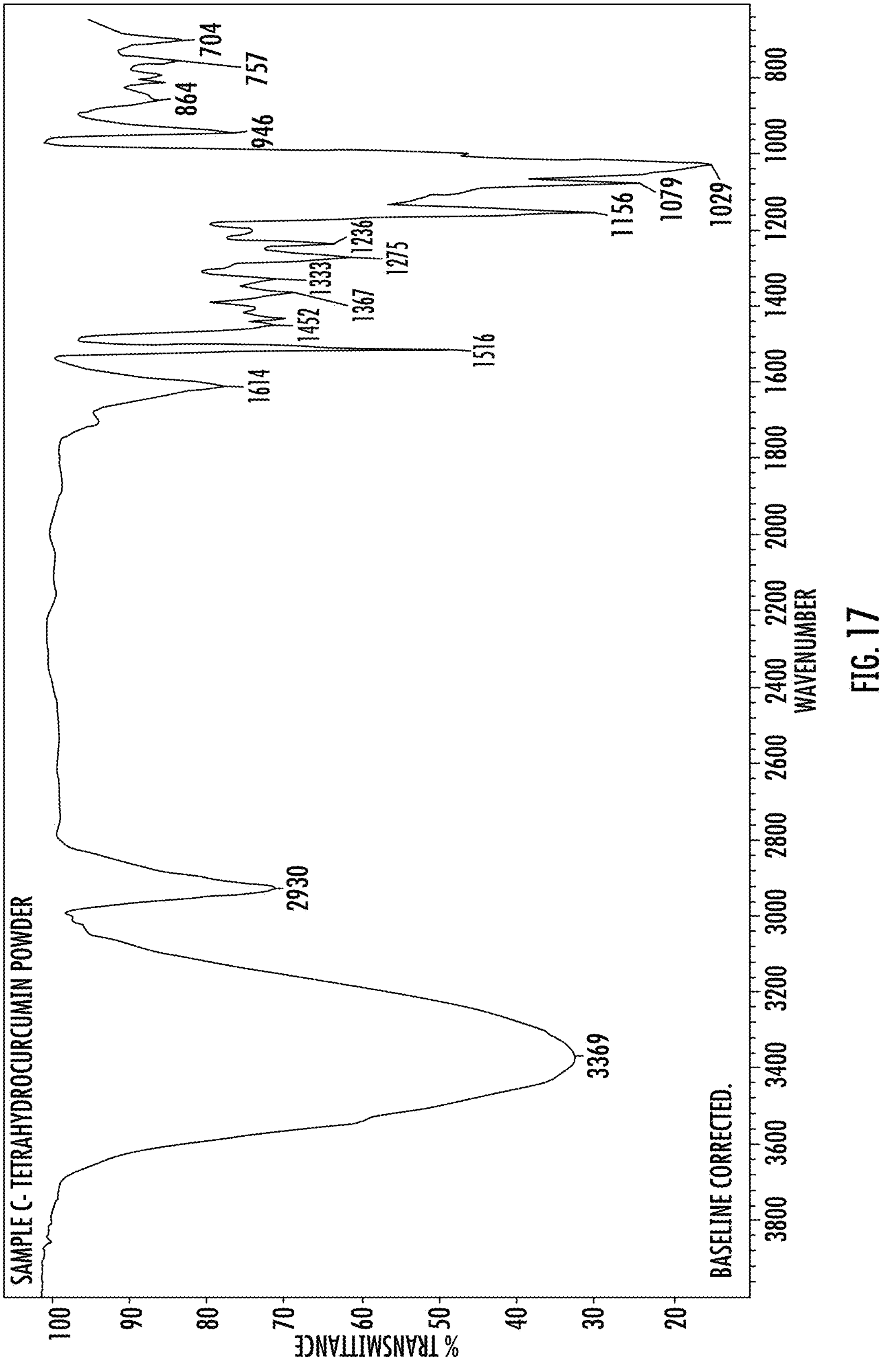
FIG. 17 is a spectra of tetrahydrocurcumin powder using FTIR.
Figure 18:
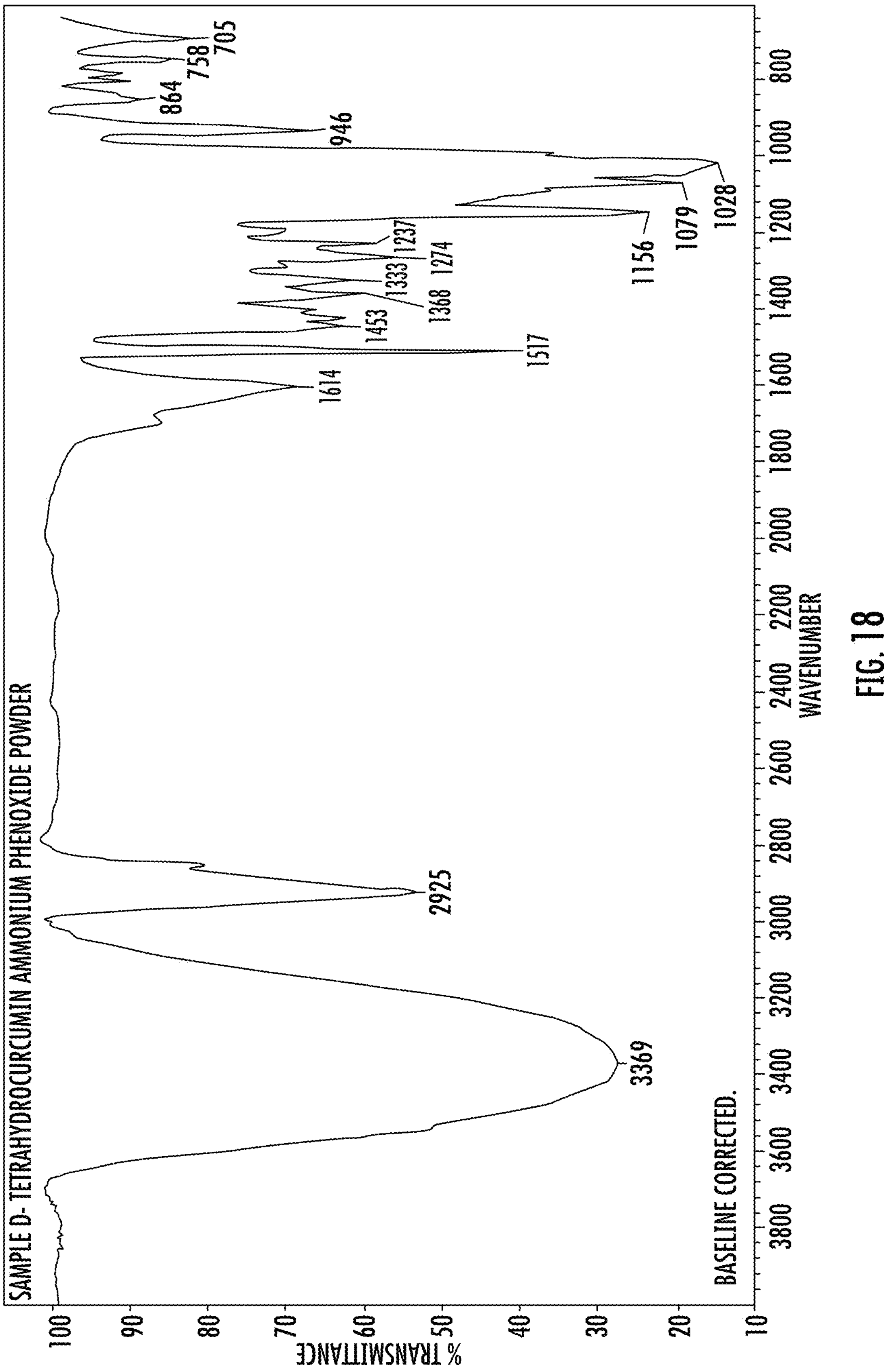
FIG. 18 is a spectra of the ammonium phenoxide of tetrahydrocurcumin using FTIR.
Figure 19:
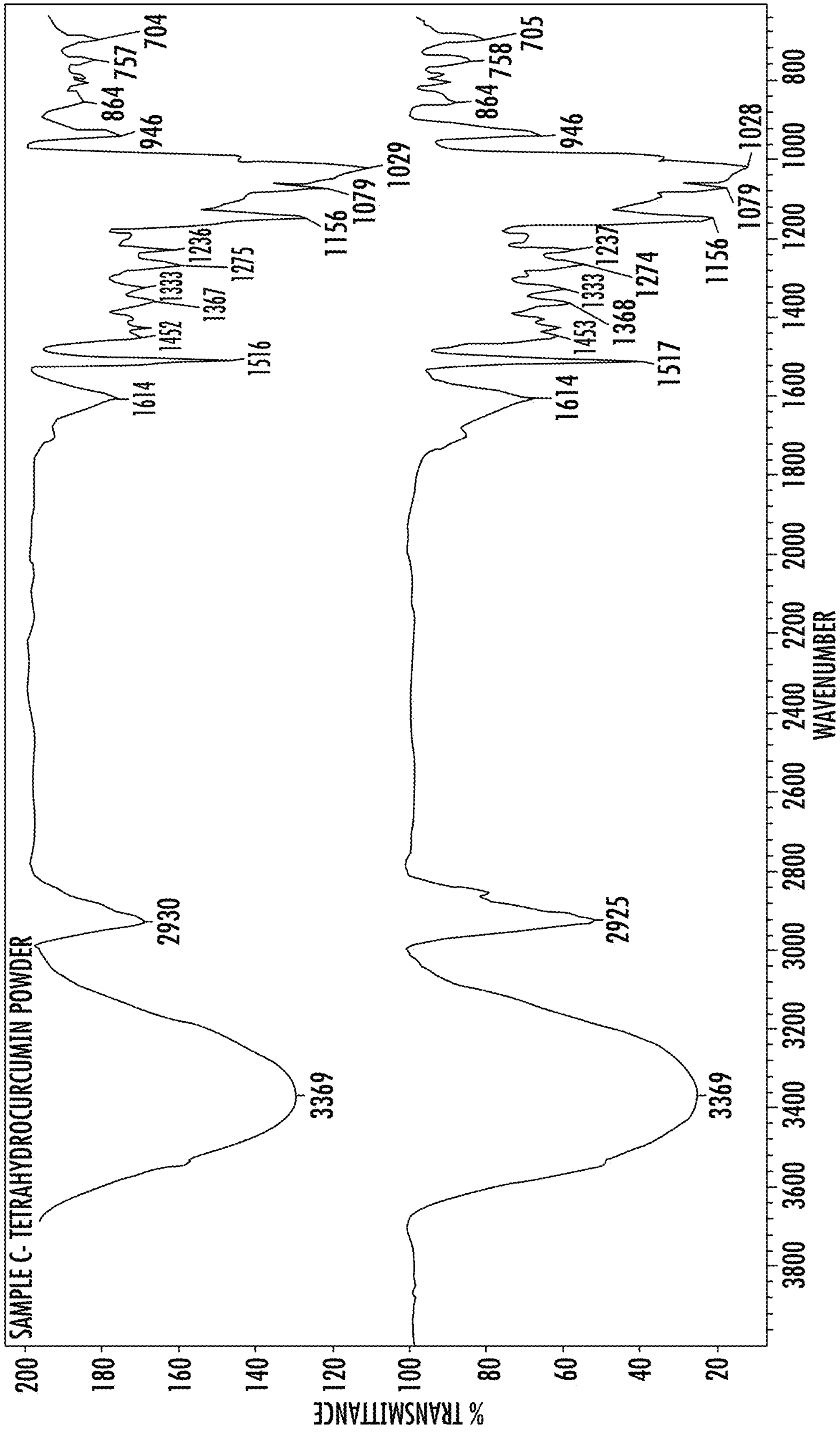
FIG. 19 depicts a plot of the tetrahydrocurcumin spectra from FIG. 19 over the ammonium phenoxide of tetrahydrocurcumin spectra from FIG. 18.
Figure 20:
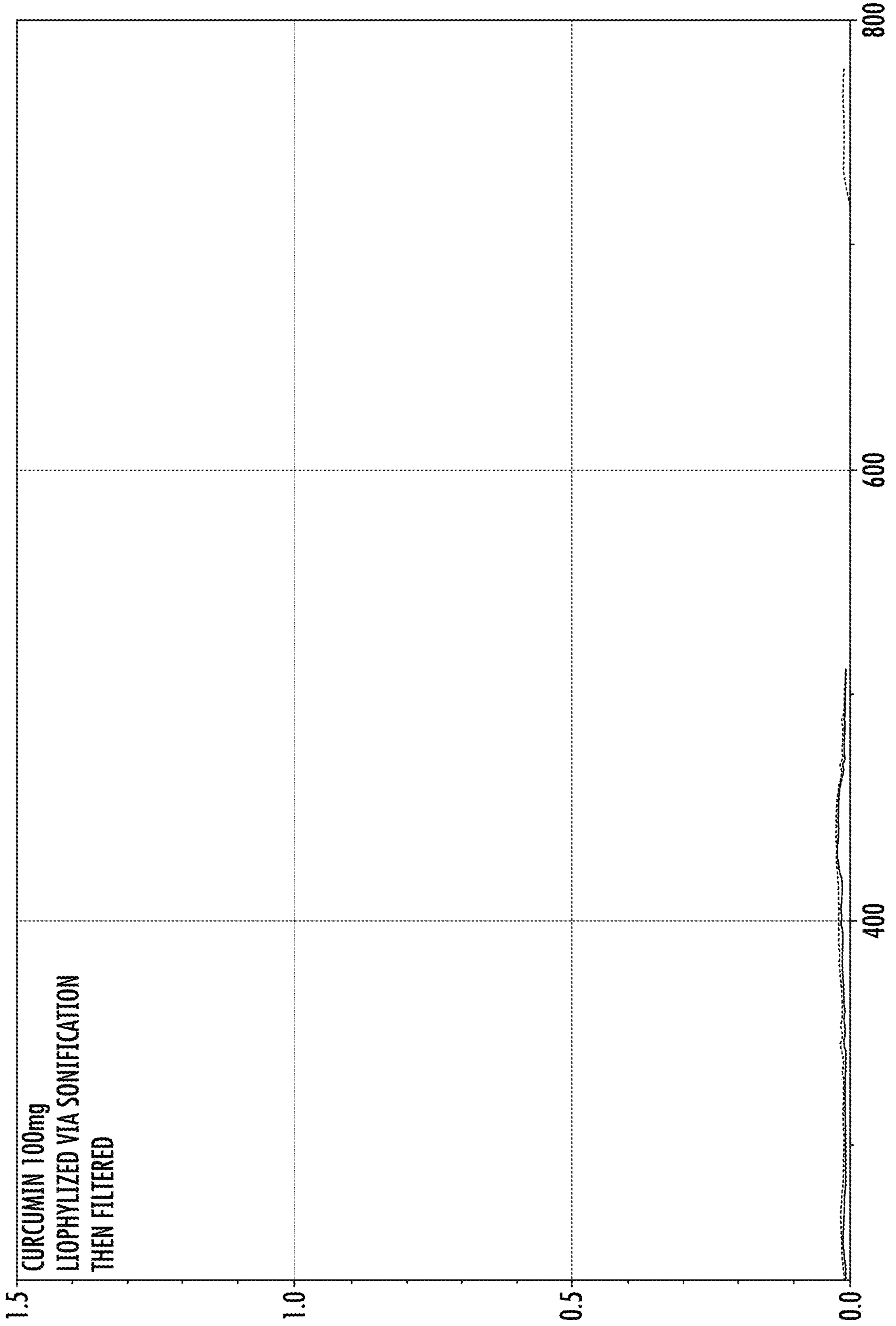
FIG. 20 depicts a graph of the absorbance of 1:10 dilution of a filtrate from mixing 100 mg curcumin in 100 ml distilled water, which was then emulsified with sonication and then filtered.
Figure 21:
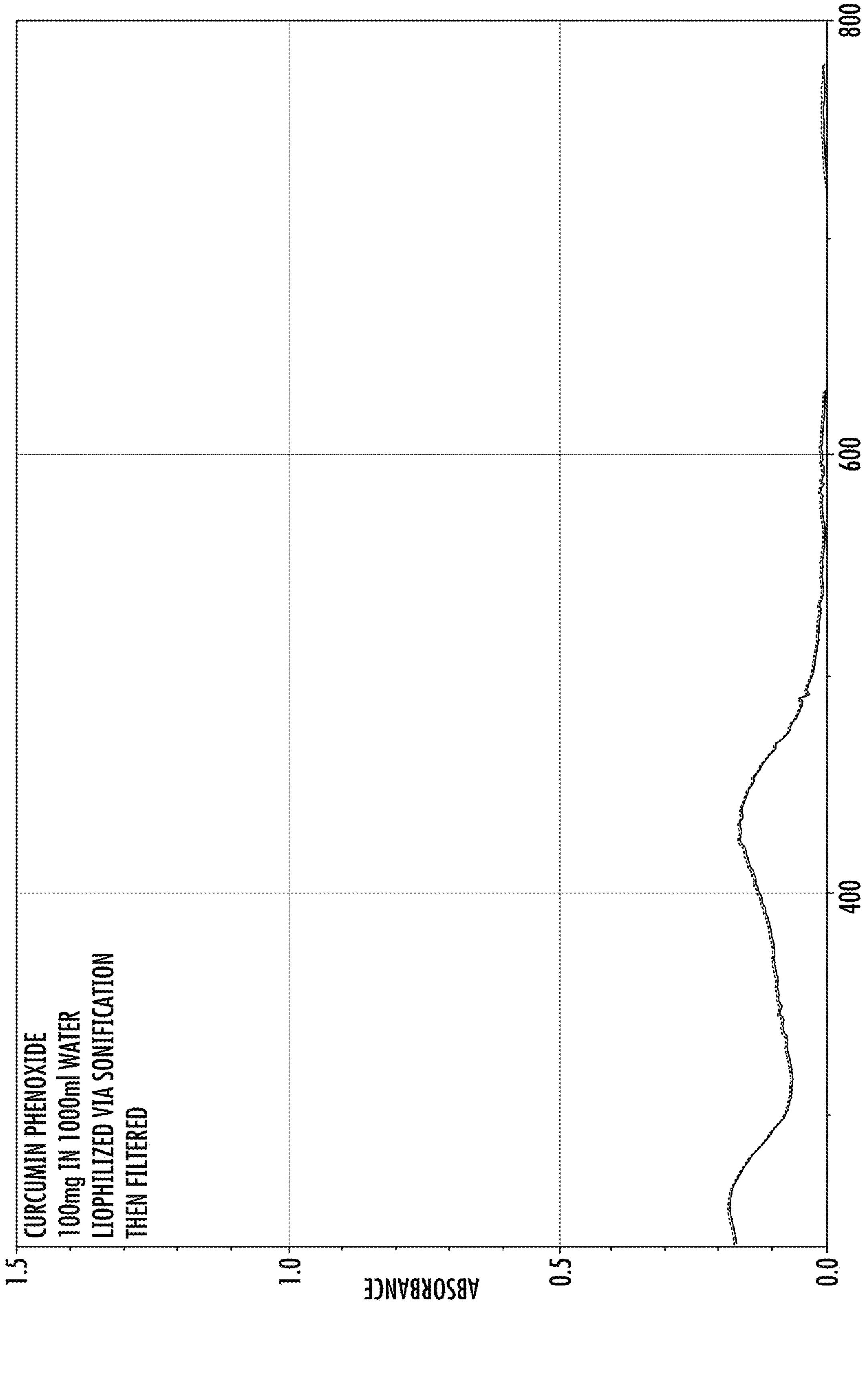
FIG. 21 depicts a graph of the absorbance of 1:10 dilution of a filtrate from mixing 100 mg ammonium phenoxide of curcumin in 100 ml distilled water, which was then emulsified with sonication and then filtered.
Figure 22:
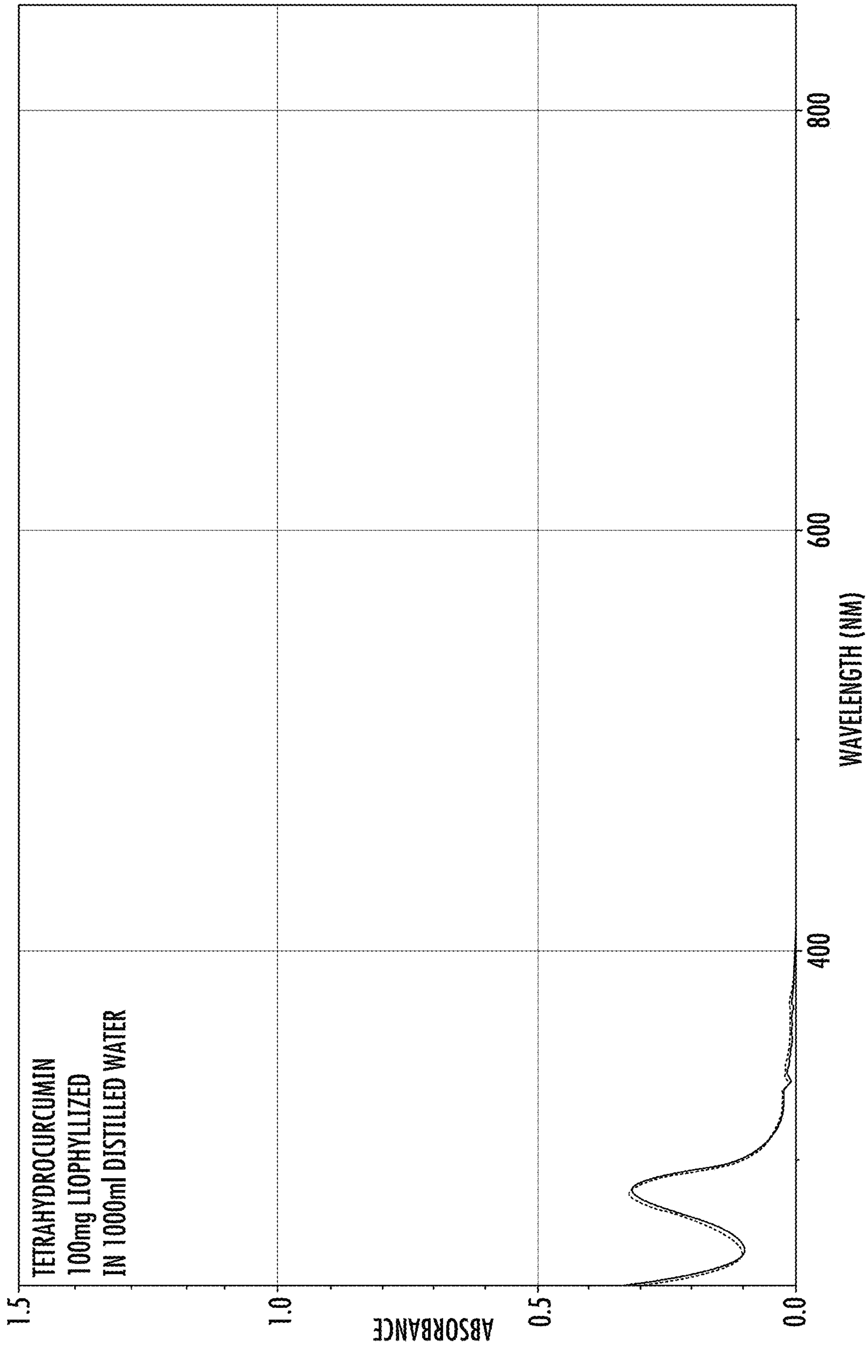
FIG. 22 depicts a graph of the absorbance of 1:10 dilution of a filtrate from mixing 100 mg tetrahydrocurcumin in 100 ml distilled water, which was then emulsified with sonication and then filtered.
Figure 23:
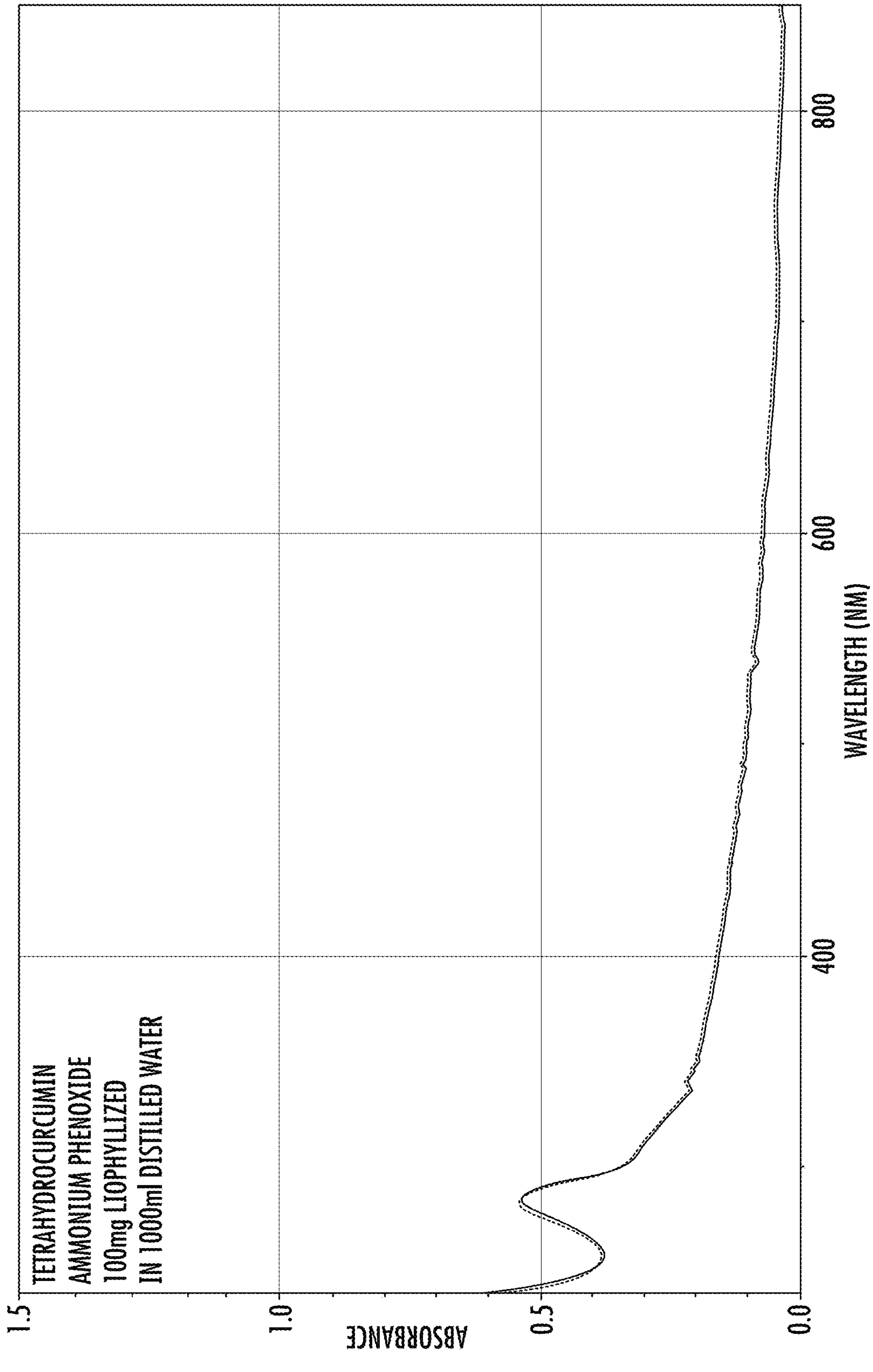
FIG. 23 depicts a graph of the absorbance of 1:10 dilution of a filtrate from mixing 100 mg ammonium phenoxide of tetrahydrocurcumin in 100 ml distilled water, which was then emulsified with sonication and then filtered.

Although curcumin is practically insoluble in water, it is even less soluble in an acidic environment. For example, the solubility of curcumin in water, Phosphate buffer, and 0.1 mol/L hydrochloric acid was 1.622, 0.310, and 0.675 μg/ml, respectively (Lu Y, Lin M, Zong J, Zong L, Zhao Z, Wang S, Zhang Z, and Han M, *Highly bioavailable curcumin preparation with a co-grinding and solvent-free process*, Food Sci Nutr. 2020 Oct. 7; 8 (12): 6415-6425. doi: 10.1002/fsn3.1930. PMID: 33312527; PMCID: PMC7723189). It was thus of interest to investigate whether the ammonium phenoxide of curcumin would also exhibit enhanced solubility in acidic pH. Therefore, 2 grams of the ammonium phenoxide of curcumin were put in 200 ml of saturated citric acid solution (pH=3). The resulting acidic solution was then passed out by a filter. The liquid that passed through the filter had the characteristic orange color of curcumin (FIG. 12). Then, 2 grams of 95% curcumin were put in 200 ml of saturated citric acid solution (pH=3). The resulting acidic solution was then passed out by a filter. The liquid that passed through the filter was, just as the water at neutral pH, totally clear (FIG. 13; the slight yellowish tint in the water is from residues from previous use of the filter). Thus, the ammonium phenoxide of curcumin exhibits increased solubility even at acidic pH.

The invention claimed is:

1. A composition comprising an ammonium phenoxide of curcumin or a curcuminoid, wherein the ammonium phenoxide of curcumin has the following structure:

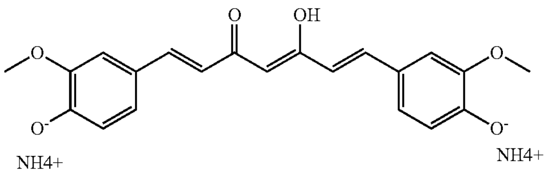

.

and the curcuminoid is selected from the group consisting of: curcumin glucuronide, tetrahydrocurcumin, curcumin sulfate, hexahydrocurcuminol, demethoxycurcumin, bisdemethoxycurcumin, and cyclocurcumin, and wherein the ammonium phenoxide of the curcumin or curcuminoid when dissolved in an aqueous solution remains dissolved in an acidic pH.

2. The composition of claim 1, further comprising a dissolution enhancer.

3. The composition of claim 2, wherein the dissolution enhancer is sodium carbonate.

4. The composition of claim 1, further comprising a dietary ingredient, a food additive, or a pharmaceutically acceptable additive.

5. The composition of claim 4, wherein the pharmaceutically acceptable additive comprises one or more of a solubilizer, an enzyme inhibiting agent, an anticoagulant, an antifoaming agent, an antioxidant, a coloring agent, a coolant, a cryoprotectant, dilutant, a hydrogen bonding agent, a flavoring agent, a flow agent, a plasticizer, a preservative, a sweetener, a thickener, and a carrier.

6. The composition of claim 4, wherein the pharmaceutically acceptable additive comprises one or more of calcium phosphate, cellulose, stearic acid, crosscarmellose cellulose, magnesium stearate, and silicon dioxide.

7. The composition of claim 1, further comprising a binder.

8. The composition of claim 1, wherein the composition is in the form of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, or a foam.

9. The composition of claim 1, further comprising a lubricant.

10. The composition of claim 9, wherein the lubricant comprises one or more of magnesium stearate, calcium stearate, talc, and colloidal silica.

11. The composition of claim 1, wherein the composition comprises 5-95% ammonium phenoxide of curcumin by weight.

12. The composition of claim 1 further comprising human saliva, human gastric juice, human enteric juice, or any combination thereof.

13. A method for forming the ammonium peroxide of the curcumin or curcuminoid according to claim 1, comprising dissolving the curcumin or curcuminoid in an ammonia solution, wherein the molar ratio of ammonia to the curcumin or curcuminoid is about 1:1 to about 2:1.

14. The method of claim 13, further comprising drying the ammonia solution comprising the dissolved curcumin or curcuminoid to produce a dried product.

15. The method of claim 14, further comprising grinding the dried product to produce a powder.

16. The method of claim 13, wherein the ammonia solution comprises about 5 wt % to about 40 wt % ammonia.

17. The composition of claim 1, wherein the acidic pH is about 3.

* * * * *